US012706192B2

(12) United States Patent
Shibuya et al.

(10) Patent No.: US 12,706,192 B2
(45) Date of Patent: Aug. 11, 2026

(54) REPORT CREATION SUPPORT DEVICE

(71) Applicant: Canon Kabushiki Kaisha, Tokyo (JP)

(72) Inventors: Masato Shibuya, Otawara (JP); Guang Yi Ong, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 325 days.

(21) Appl. No.: 18/163,952

(22) Filed: Feb. 3, 2023

(65) Prior Publication Data

US 2023/0253083 A1 Aug. 10, 2023

(30) Foreign Application Priority Data

Feb. 4, 2022 (JP) ................................ 2022-016500

(51) Int. Cl.
*G16H 15/00* (2018.01)
*G06T 7/00* (2017.01)
(Continued)

(52) U.S. Cl.
CPC ........... *G16H 15/00* (2018.01); *G06T 7/0016* (2013.01); *G06T 7/70* (2017.01); *G16H 30/40* (2018.01);
(Continued)

(58) Field of Classification Search
CPC ........ G16H 15/00; G16H 30/40; G16H 50/20; G16H 30/20; G06T 7/0016; G06T 7/70; G06T 2207/10132; G06T 2207/30068; G06T 2207/30096; G06T 7/0012; G06T 7/12; G06T 7/136; G06T 7/73; G06T 2207/20104
See application file for complete search history.

(56) References Cited

U.S. PATENT DOCUMENTS 8,452,613 B2 5/2013 Meinel et al.
9,050,557 B1 6/2015 Leppin et al.
(Continued)

FOREIGN PATENT DOCUMENTS

JP 10-108859 A 4/1998
JP 2011-522655 8/2011
(Continued)

OTHER PUBLICATIONS

Office Action issued on Nov. 21, 2025, in corresponding Japanese Application No. 2022-016500, 14 pages.

*Primary Examiner* — Atiba O Fitzpatrick
(74) *Attorney, Agent, or Firm* — Oblon, McClelland, Maier & Neustadt, L.L.P.

(57) ABSTRACT

According to one embodiment, a report creation support device includes an identifying module and a report creating module. The identifying module is configured to, when receiving an input selecting a reading order related to a first medical image in which a patient's site is captured by a first modality, specify a predetermined region of the first medical image as a region of interest, and identify a second medical image corresponding to the specified region of interest from among second medical images in which the patient's site is captured by a second modality which is different from the first modality. The report creating module is configured to attach the first medical image and the identified second medical image to a predetermined region of a reading report created for the reading order.

9 Claims, 14 Drawing Sheets

(51) Int. Cl.
*G06T 7/70* (2017.01)
*G16H 30/40* (2018.01)

(52) U.S. Cl.
CPC ............... *G06T 2207/10132* (2013.01); *G06T 2207/30068* (2013.01); *G06T 2207/30096* (2013.01)

(56) References Cited

U.S. PATENT DOCUMENTS

2005/0089205 A1* 4/2005 Kapur .................... A61B 8/483 382/128
2007/0274585 A1* 11/2007 Zhang .................... G16H 30/20 382/132
2011/0123079 A1* 5/2011 Gustafson .............. G16H 15/00 707/769
2011/0137132 A1* 6/2011 Gustafson ............ A61B 5/4312 600/300
2014/0082542 A1* 3/2014 Zhang .................... G16H 30/40 715/771
2014/0149407 A1* 5/2014 Qian ....................... G06F 16/35 707/758
2014/0219500 A1* 8/2014 Moehrle ............... G06T 7/0014 382/103
2015/0139518 A1 5/2015 Oohashi et al.
2015/0262014 A1* 9/2015 Iwamura ................ G16H 50/20 382/128
2019/0325573 A1* 10/2019 Bernard ................. A61B 8/085
2022/0036545 A1* 2/2022 St. Pierre ............. A61B 8/4416
2023/0103969 A1* 4/2023 St. Pierre .............. G06T 7/0014 382/128
2023/0124481 A1* 4/2023 St. Pierre ............... A61B 8/085 600/427

FOREIGN PATENT DOCUMENTS

JP 2014-14489 1/2014
JP 2015-100661 6/2015
JP 2017-99769 6/2017
JP 2018-33657 3/2018

* cited by examiner

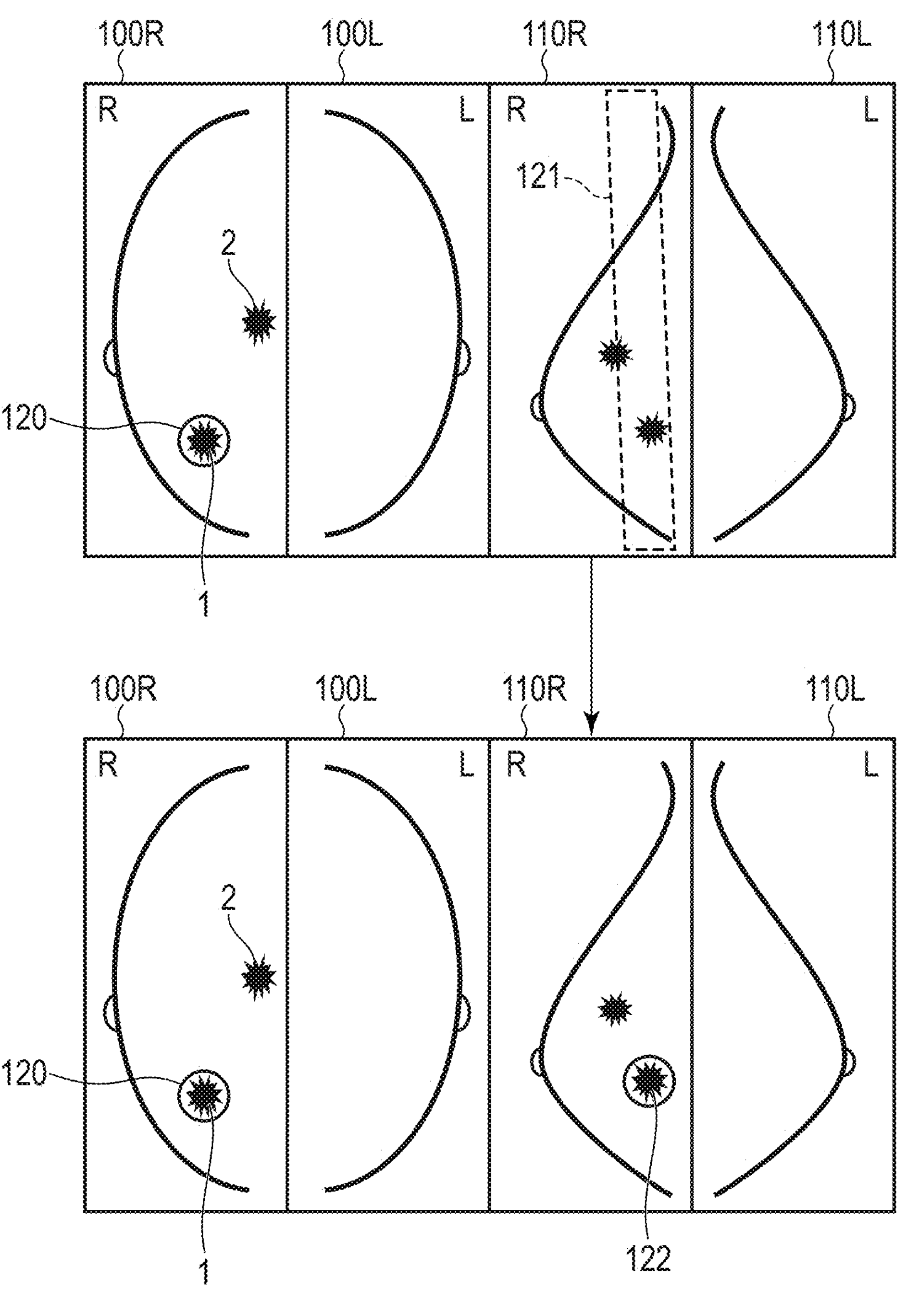
F I G. 4

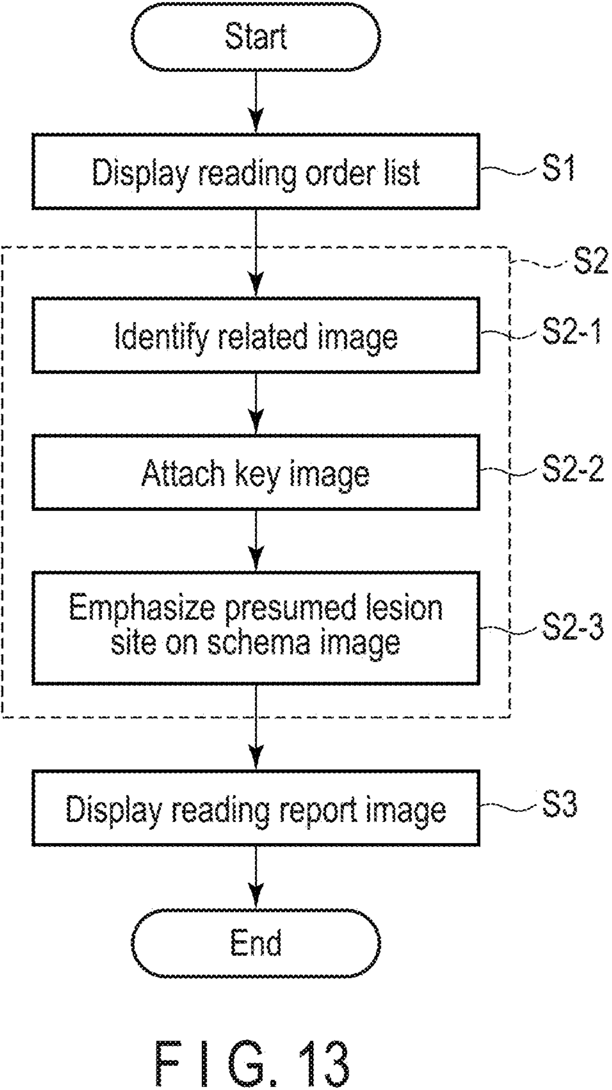
F I G. 13

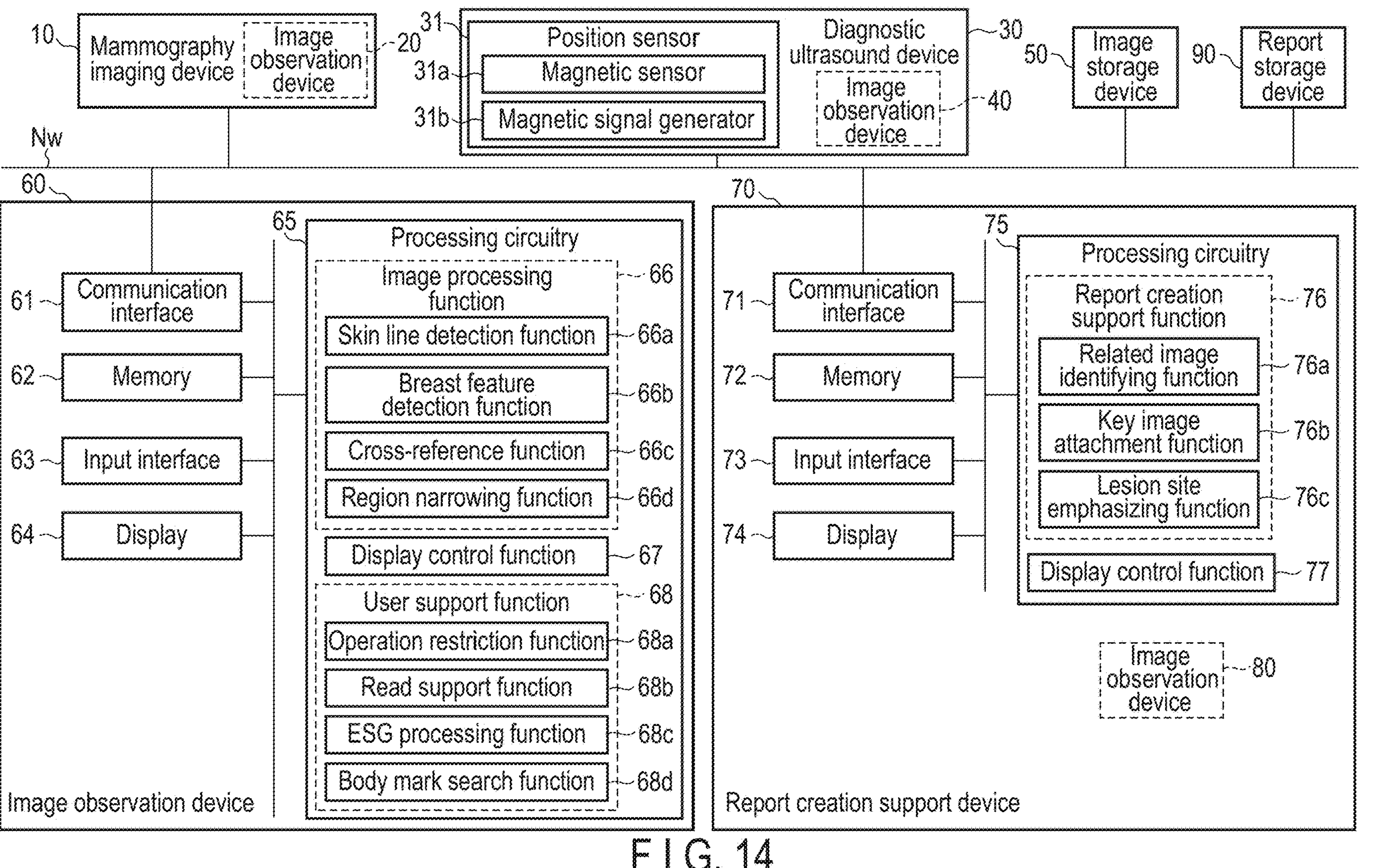
F I G. 14

REPORT CREATION SUPPORT DEVICE

CROSS-REFERENCE TO RELATED APPLICATIONS

This application is based upon and claims the benefit of priority from Japanese Patent Application No. 2022-016500, filed Feb. 4, 2022, the entire contents of which are incorporated herein by reference.

FIELD

Embodiments described herein relate generally to a report creation support device.

BACKGROUND

During breast cancer screening, images of left and right breasts of a patient are captured by a mammography imaging device in a state where the left and right breasts are individually compressed in a first direction, and, also, in a state where the left and right breasts are individually compressed in a second direction. A total of four pieces of mammogram images, which are a first direction image of the left breast, a first direction image of the right breast, a second direction image of the left breast, and a second direction image of the right breast, are obtained by the imaging. For example, the first direction may be a craniocaudal projection (CC) and the second direction may be a mediolateral oblique projection (MLO). Also, the first direction may be the mediolateral oblique projection (MLO) and the second direction may be the craniocaudal projection (CC), for example. In any case, in the following examples, a CC-directed image is also referred to as a CC image and an MLO-directed image is also referred to as an MLO image.

These four mammogram images are basically read in pairs on the left and right sides. For example, the CC image and MLO image of the left breast are read in pairs, and the CC image and MLO image of the right breast are read in pairs.

In recent years, in consideration of patients with dense mammary glands (dense breasts), reading is performed not only with mammogram images captured by mammography imaging devices, but also with ultrasound images captured by diagnostic ultrasound devices.

While images to be read are becoming more diverse, a radiologist must manually select the images to be read and manually input reading results for the images to create a reading report. This is a significant burden for the radiologist. Therefore, technology that can reduce this burden is being desired.

BRIEF DESCRIPTION OF THE DRAWINGS

FIG. 4 is a schematic diagram illustrating an example of a region narrowing function in the embodiment.

FIG. 13 is a flowchart illustrating a series of processing procedures executed by a report creation support device according to the embodiment.

FIG. 14 is a block diagram showing a configuration of a medical information processing system equipped with a report creation support device according to a second embodiment.

DETAILED DESCRIPTION

In general, according to one embodiment, a report creation support device includes an identifying module and a report creating module. The identifying module is configured to, when receiving an input selecting a reading order related to a first medical image in which a patient's site is captured by a first modality, specify a predetermined region of the first medical image as a region of interest, and identify a second medical image corresponding to the specified region of interest from among second medical images in which the patient's site is captured by a second modality which is different from the first modality. The report creating module is configured to attach the first medical image and the identified second medical image to a predetermined region of a reading report created for the reading order.

An embodiment of a report creation support device will be described in detail below with reference to the drawings.

Note that, the disclosure is only an example, and any modification that can be easily conceived by a person skilled in the art, while maintaining the main purpose of the invention, is naturally included in the scope of the invention. In the present specification and each drawing, components that perform the same or similar functions as those described above with respect to the drawings already described are denoted by the same reference symbols, and redundant detailed descriptions may be omitted.

First Embodiment

Figure 1:
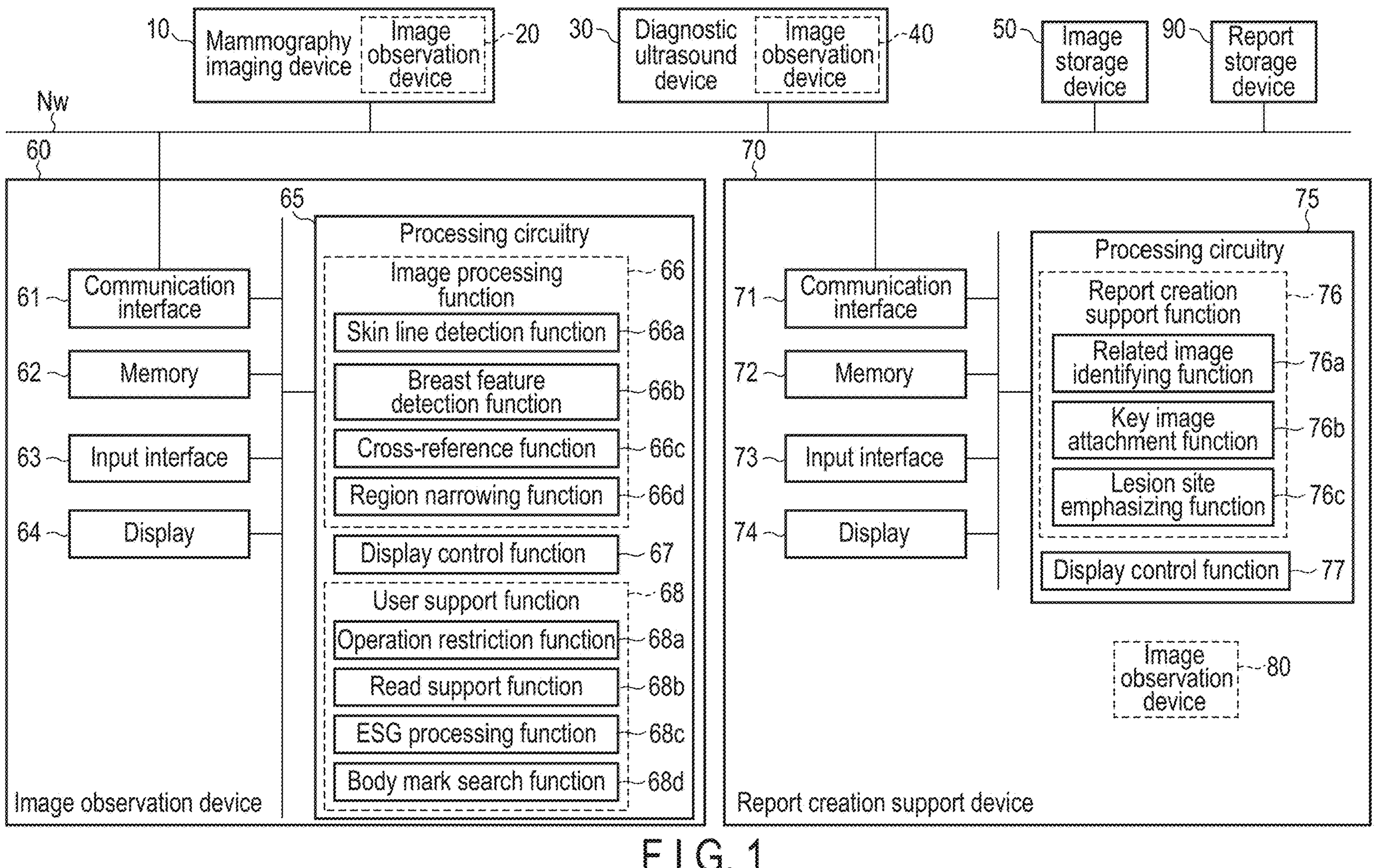
FIG. 1 is a block diagram showing a configuration of a medical information processing system equipped with a report creation support device according to a first embodiment.

FIG. 1 is a block diagram showing a configuration of a medical information processing system equipped with a report creation support device according to a first embodiment. In this medical information processing system, a mammography imaging device 10, a diagnostic ultrasound device 30, an image storage device 50, an image observation device 60, a report creation support device 70, and a report storage device 90 can communicate via a network Nw. Note that the image observation device 60 may be mounted on the mammography imaging device 10 as an image observation device 20 as shown in broken lines. In other words, processing circuitry (not shown) of the mammography imaging device 10 may operate to realize each function of the image observation device 20 in addition to each function for mammography imaging. Alternatively, the image observation device 60 may be mounted on the diagnostic ultrasound device 30 as an image observation device 40 as shown in broken lines. In other words, processing circuitry (not shown) of the diagnostic ultrasound device 30 may operate to realize each function of the image observation device 60 in addition to each function for ultrasound diagnosis. Alternatively, the image observation device 60 may be mounted on the report creation support device 70 as an image observation device 80 as shown in broken lines. In other words, processing circuitry of the report creation support device 70 may operate to realize each function of the image observation device 60 in addition to each function for creating a reading report.

Here, the mammography imaging device 10 is a device capable of capturing mammogram images which are medical images. Specifically, the mammography imaging device 10 captures images of left and right breasts of a patient (specimen) individually compressed in a first direction, and, also, captures images of the left and right breasts individually compressed in a second direction. A total of four mammogram images, which are a first direction image of the left breast, the first direction image of the right breast, a second direction image of the left breast, and the second direction image of the right breast, are obtained by the imaging. Hereafter, the first direction image of the left breast and the first direction image of the right breast are also referred to as a "first mammogram image", respectively. Similarly, the second direction image of the left breast and the second direction image of the right breast are also referred to as a "second mammogram image". In a case where the "first mammogram image" and the "second mammogram image" are not distinguished, each of the four images is also referred to as a "mammogram image". As the first and second directions, for example, among a craniocaudal projection (CC), a mediolateral projection (ML), a mediolateral oblique projection (MLO), etc., a CC direction and an MLO direction or a CC direction and an ML direction can be used as appropriate. In the present embodiment, the CC and MLO directions are used as an example. In this case, a "CC direction image" and an "MLO direction image" are also referred to as a "CC image" and an "MLO image", respectively.

The diagnostic ultrasound device 30 is a device capable of capturing ultrasound images, which are medical images, by transmitting and receiving ultrasound waves with an ultrasound probe (not shown) placed at a desired position on a patient's breast. The diagnostic ultrasound device 30 may also be capable of guiding the ultrasound probe to a position in the breast by displaying a mammogram image or a body mark of the breast. The diagnostic ultrasound device 30 may also comprise a position sensor of the ultrasound probe so that a position of the ultrasound probe may be displayed on a body mark of the breast.

The image storage device 50 is a storage device that stores multiple types of image data captured by the mammography imaging device 10 and the diagnostic ultrasound device 30. The image storage device 50 may also be referred to as an image server device. Each image data is a so-called DICOM (Digital Imaging Communications and Medicine) image file, which is a standard in the field of image examination, and has ancillary information. The ancillary information is configured by a plurality of ancillary items. The ancillary information always includes a patient ID to identify the patient. In addition to the patient ID, the ancillary information may include a modality ID to identify the mammography imaging device 10 and the diagnostic ultrasound device 30, imaging date information indicating the date of imaging, imaging site information indicating an imaging site, type information indicating whether the image data is a morphological image or a functional image, image collection conditions (scanning conditions, imaging conditions), contrast agent information (contrast agent type, injection amount, injection time, etc.), examination orders (examination site, purpose of examination, etc.), examination ID, and series ID. In the present embodiment, the ancillary information includes the various ancillary items described above; however, is not limited to these items and may further include, for example, an image ID that is assigned to each image data.

The image observation device 60 comprises a communication interface 61, a memory 62, an input interface 63, a display 64, and processing circuitry 65. The image observation device 60 includes various functions to support reading of image data stored in the image storage device 50.

The communication interface 61 is a circuit for connecting the image observation device 60 to the network Nw and communicating with other devices. For example, a network interface card (NIC) can be used as the communication interface 61. In the following, a description on the communication interface 61 intervening in the communication between the image observation device 60 and other devices is omitted.

The memory 62 is configured by a memory storing electrical information such as a read only memory (ROM), a random access memory (RAM), a hard disk drive (HDD), and an image memory, and peripheral circuits such as a memory controller and a memory interface associated with these memories. The memory 62 stores an image observation program for the present image observation device, mammogram images, body marks, ultrasound images, and various data groups such as imaging position information of the ultrasound images.

The input interface 63 is realized by a trackball, a switch button, a mouse, a keyboard, a touch pad (or a track pad) for performing input operations by touching an operation surface, and a touch panel display (or a touch screen) in which a display screen and a touch pad are integrated and the like to input various instructions, commands, information, selections, and settings from an operator (user) to a main unit of the image observation device. The input interface 63 is connected to the processing circuitry 65, converts input operations received from a user into electrical signals, and outputs the input operations received from the user to the processing circuitry 65. In this case, the input interface 63 may display a user interface (GUI: Graphical User Interface) on the display 64 for the user to input various instructions by physical operation components such as a mouse or a keyboard. Note that, in the present specification, the input interface 63 is not only limited to those with physical operation components. For example, processing circuitry of an electrical signal that receives electrical signals corresponding to input operations from an external input device provided separately from the device, and outputs these electrical signals to the processing circuitry 65 is also included in the example of the input interface 63. In the following description, an "operation of the input interface 63 by the user" is also referred to as a "user operation".

The display 64 is configured by a display body that displays medical images, etc., internal circuits that supply display signals to the display body, and peripheral circuits such as connectors and cables that connect the display and the internal circuits. The display 64 can display, for example, a first mammogram image in the memory 62, and a schematic diagram and a predetermined range each generated and calculated by the processing circuitry 65.

The processing circuitry 65 reads the image observation program stored in the memory 62 based on an instruction input by the user via the input interface 63, and controls the image observation device 60 according to the program. For example, the processing circuitry 65 is a processor that realizes each function of the image observation device 60 in accordance with the image observation program read from the memory 62. Here, each function includes, for example, an image processing function 66, a display control function 67, and a user support function 68. The image processing function 66 includes, for example, a skin line detection function 66*a*, a breast feature detection function 66*b*, a cross-reference function 66*c*, and a region narrowing function 66*d*. The user support function 68 includes, for example, an operation restriction function 68*a*, a read support function 68*b*, an ESG processing function 68*c*, and a body mark search function 68*d*. An ESG is an abbreviation for Echo Scan Guide, which will be described later. Note that, each function may be realized by being distributed across multiple processors as appropriate. For example, among each of the functions, the skin line detection function 66*a*, the breast feature detection function 66*b*, and the cross-reference function 66*c* may be performed by a first processor, and the remaining functions may be performed by a second processor. Alternatively, each function may be executed by an external cloud or the image observation devices 20, 40, and 80 in other devices, as appropriate. For example, among each of the functions, the image processing function 66 may be executed by an external cloud or the processing circuit (not shown) of the image observation device 20 in the mammography imaging device 10, and the remaining display control function 67 and user support function 68 may be executed by the processing circuitry 65. Alternatively, among each of the functions, the image processing function 66 may be executed by the processing circuitry 65, and the remaining display control function 67 and user support function 68 may be executed by the processing circuit (not shown) of the image observation device 40 in the diagnostic ultrasound device 30. In addition, the skin line detection function 66*a*, the breast feature detection function 66*b*, the region narrowing function 66*d*, and the user support function 68 are optional additional items and may be omitted. In the case where the skin line detection function 66*a* and the breast feature detection function 66*b* are omitted, for example, the skin line and feature may be indicated on the mammogram image by the user operation.

Next, the skin line detection function 66*a*, the breast feature detection function 66*b*, the cross-reference function 66*c*, and the region narrowing function 66*d* included in the image processing function 66 are described in turn.

The skin line detection function 66*a* detects skin lines (breast contours) in mammogram images. The skin line detection function 66*a* may, for example, determine a threshold value based on a histogram of pixel values in a mammogram image and detect skin lines using the threshold value. The skin line detection function 66*a* may also detect skin lines using, for example, an edge enhancement filter or a Sobel filter.

The breast feature detection function 66*b* detects breast features (breast ends, nipples, and chest wall) from the mammogram image in which skin lines are detected. The breast feature detection function 66*b* may, for example, bring a vertical or diagonal straight line close to the skin line and detect breast features according to a position where the straight line and the skin line come in contact. The breast feature detection function 66*b* may also detect other breast features based on the previously detected breast features, for example.

The cross-reference function 66*c* selects lesion candidates from the first mammogram image obtained by imaging the patient's breast with the breast compressed in the first direction. The selection of lesion candidates may be performed, for example, in response to the user operation or in response to the coordinates of lesion candidates included in the results of computer-aided detection (CAD). Alternatively, the selection of lesion candidates may be performed in response to the user operation on the CAD results. The "lesion candidates" may also be referred to as "lesions". The cross-reference function 66*c* also calculates a target region corresponding to the position of the lesion candidate in the second mammogram image obtained by imaging the breast in a state where it is compressed in the second direction, which is different from the first direction. The position of the lesion candidate is the coordinates of the selected lesion candidate (coordinates in the first mammogram image). In the present embodiment, as mentioned above, the CC and MLO directions are used as an example of the first and second directions. Here, the first direction may be the CC direction and the second direction may be the MLO direction. Conversely, the first direction may be the MLO direction and the second direction may be the CC direction. In the same way as above, the CC direction image is also referred to as the CC image, and the MLO direction image is also referred to as the MLO image.

Figure 2:
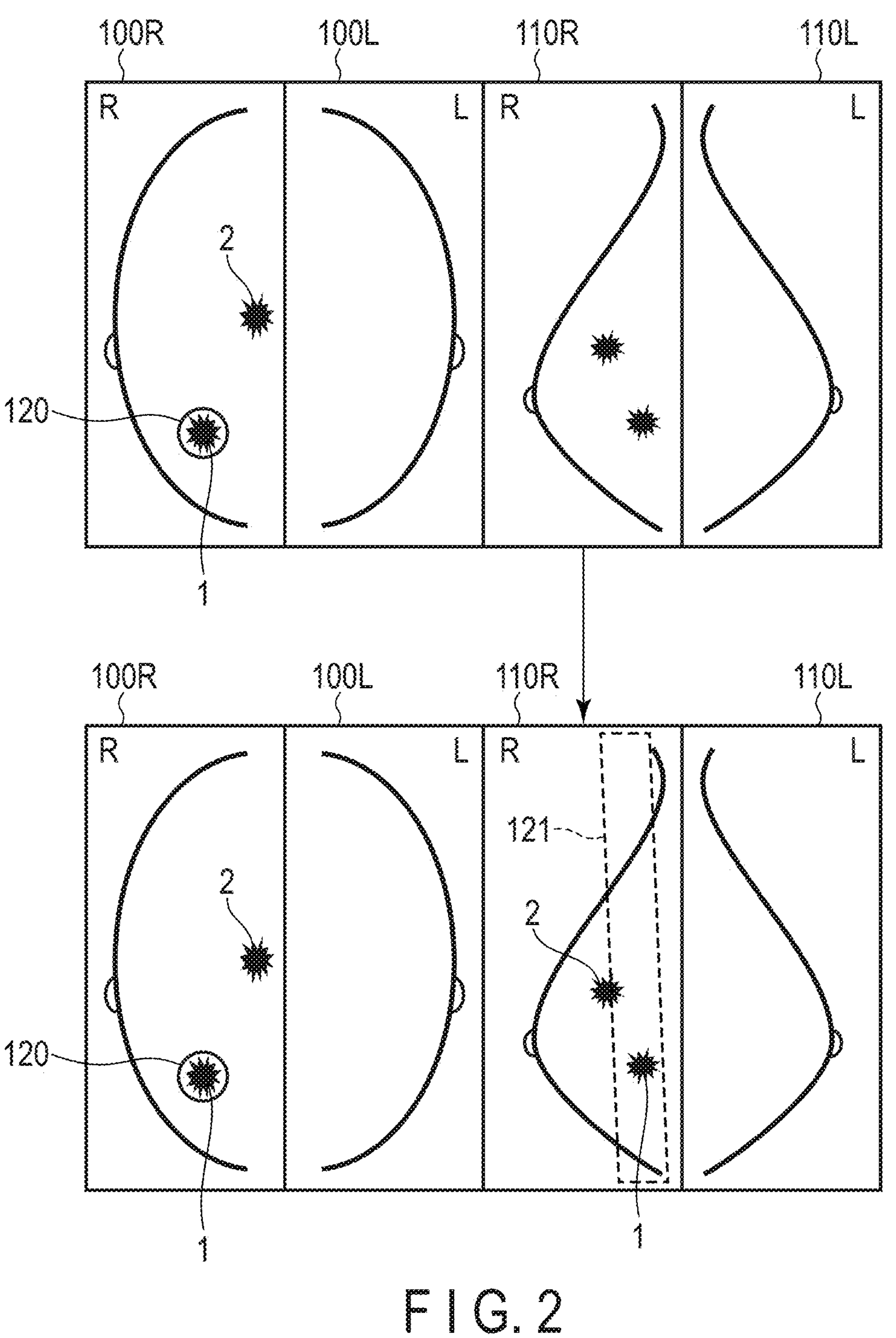
FIG. 2 is a schematic diagram illustrating an example of a cross-reference function in the embodiment.

An example of a case where, for example, the first direction is the CC direction and the second direction is the MLO direction is shown in FIG. 2. As shown in the upper row of FIG. 2, suppose that a CC image 100R of the right breast, a CC image 100L of the left breast, an MLO image 110R of the right breast, an MLO image 110L of the left breast are displayed, and two lesion candidates are seen in the CC image 100R and the MLO image 110R of the right breast. In this case, the cross-reference function 66*c*, in response to, for example, a user operation, selects a lesion candidate 120 from among lesion candidates 1 and 2 of the CC image 100R of the right breast by encircling the lesion candidate 1. Then, as shown in the lower row of FIG. 2, the cross-reference function 66*c* calculates a target region 121 corresponding to the lesion candidate 1 in the MLO image 110R of the right breast.

Figure 3:
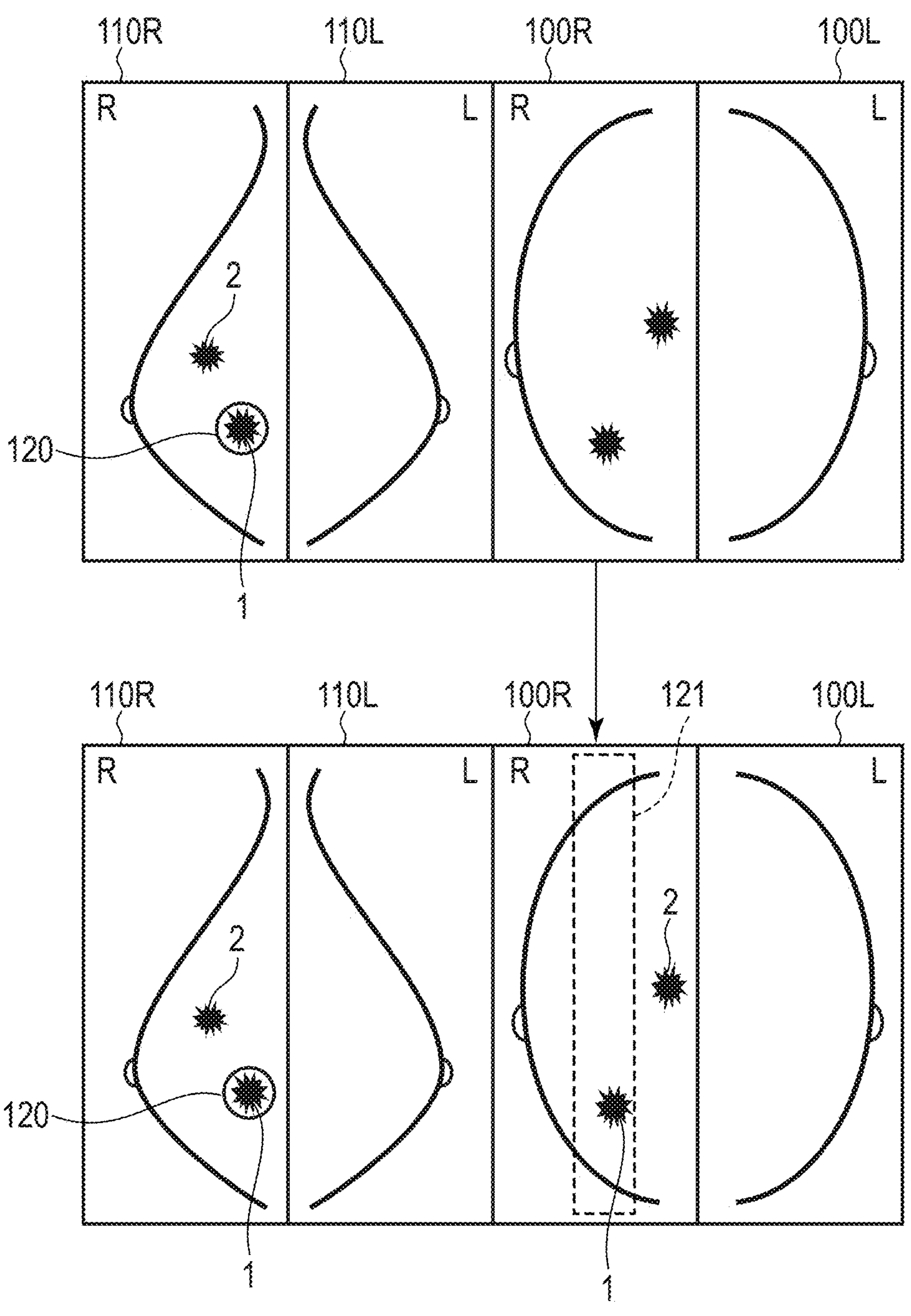
FIG. 3 is a schematic diagram illustrating another example of the cross-reference function in the embodiment.

Also, an example of a case where, for example, the first direction is the MLO direction and the second direction is the CC direction is shown in FIG. 3. As shown in the upper row of FIG. 3, suppose that the MLO image 110R of the right breast, the MLO image 110L of the left breast, the CC image 100R of the right breast, and the CC image 100L of the left breast are displayed, and two lesion candidates are seen in the MLO image 110R and CC image 100R of the right breast. In this case, the cross-reference function 66*c*, in response to, for example, a user operation, selects a lesion candidate 120 from among lesion candidates 1 and 2 of the MLO image 110R of the right breast by encircling the lesion candidate 1. Then, as shown in the lower row of FIG. 3, the cross-reference function 66*c* calculates a target region 121 corresponding to the lesion candidate 1 in the CC image 100R of the right breast.

Figure 5:
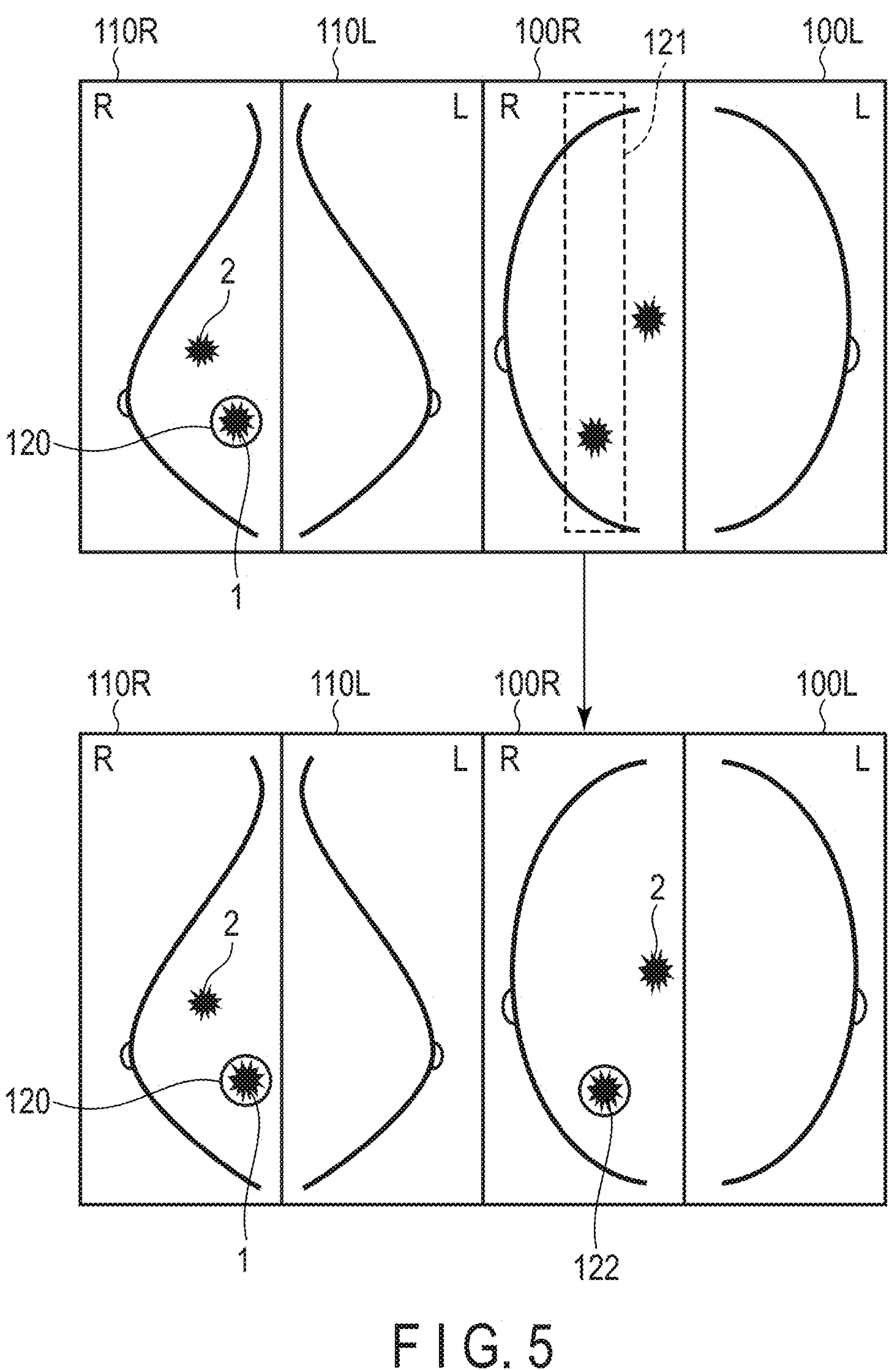
FIG. 5 is a schematic diagram illustrating an example of the region narrowing function in the embodiment.

The region narrowing function 66*d*, based on a value of the lesion candidate or a specific value, narrows down a lesion candidate region corresponding to the value of the lesion candidate from the target region. Here, the specific value may be a preset value or a value instructed by the user, and the value may be a pixel value or a range of pixel values. As shown in FIG. 4, for example, such a region narrowing function 66*d* narrows down a lesion candidate region 122 from the target region 121 of the MLO image 110R based on the value of the lesion candidate 1 of the CC image 100R. Also, for example, as shown in FIG. 5, the region narrowing function 66*d* narrows down the lesion candidate region 122 from the target region 121 of the CC image 100R based on the value of the lesion candidate 1 of the MLO image 110R.

Furthermore, in a case where multiple regions are obtained as such lesion candidate region from the target region, the region narrowing function 66*d* may narrow down the region with the highest priority among the multiple regions as the lesion candidate region. Here, as a method of assigning priority, for example, any one of the following (a) to (d) or multiple combinations thereof may be used, as appropriate.

(a) Level of relevance: The highest priority is given to a lesion with the smallest difference between the lesion/nipple distance in the second mammogram image and the lesion/nipple distance in the first mammogram image according to a calculation formula. This is because lesions with the most similar nipple distances between mammograms captured in different directions are assumed to be the same lesion. Therefore, for example, based on the calculation formula, the lesion with the closest distance to the nipple is given higher priority (because it has high relevance). Specifically, for example, the region narrowing function 66*d* may assign the highest priority to a distance closest to a distance between the nipple and the lesion candidate in the first mammogram image among a plurality of distances between the nipple and the plurality of regions in the second mammogram image.

(b) Difference in tone: A higher priority is given to a lesion with closer difference in tone among the plurality of regions. In this case, it is preferable to compare the difference in tone after leveling tones between images. Alternatively, the difference in tone may be compared by adjusting the tone by dose, current, pressure, and breast thickness obtained from a header of the images.

(c) Similarity in size: The highest priority is given to a size closest to the size of the target region among sizes of multiple regions. The size to be compared is not limited to the size obtained from the image, but may also be a size that takes into account a rigid transformation of the breast.

(d) Position in image: Priority may be given in ascending or descending order in the direction from the center toward the outer side of the breast in the image. Alternatively, priority may be given in ascending or descending order in the direction from the top toward the bottom of the breast in the image.

The display control function 67 displays images based on various image data generated by the image processing function 66 on the display 64 that serves as a display unit. Specifically, for example, the display control function 67 controls the display 64 so as to display a first mammogram image clearly showing the lesion candidate selected by the image processing function 66 and a second mammogram image that includes the target region calculated by the image processing function 66 in an identifiable state. Here, the "identifiable state" is a state in which the target region is identified by some kind of method. The method is not limited to a method of clearly indicating the target region by means of framing, changing colors, or trimming, etc., and may be a method showing the target region only when a button is operated, etc. The display control function 67 also controls the display 64 to display a third mammogram image, which is the second mammogram image in which the lesion candidate region is clearly shown in a display region different from the first mammogram image and the second mammogram image. The display control function 67 also controls the display 64 to display an image based on the processing results by the user support function 68.

Subsequently, the operation restriction function 68*a*, the reading support function 68*b*, the ESG processing function 68*c*, and the body mark search function 68*d* included in the user support function 68 are described in turn.

From among operations on the mammogram images clearly showing the lesion candidate regions, the operation restriction function 68*a* accepts operations on the lesion candidate regions while ignoring operations on regions different from the lesion candidate regions. In other words, the operation restriction function 68*a* limits operations on mammogram images including lesion candidate regions to only the operations on the lesion candidate region. Here, the operation on the lesion candidate region may be an operation for reading the lesion candidate region. For example, the operation for reading may be one of the following operations: changing the tone of the lesion candidate region, changing the size of the lesion candidate region, adding information on the lesion candidate region, clicking on the lesion candidate region, and cutting out the lesion candidate region. The operation for adding the information may be, for example, an operation for selecting a lesion candidate region in the first mammogram image, then selecting the lesion candidate region in the second mammogram image, and adding the information to the lesion candidate region. The information to be added may include, for example, at least one of the results of size measurement of the lesion candidate, annotation, description of findings, and analysis results. The click operation may also serve as the operation for changing the tone or size, the operation for adding the information, or the operation for the cutting out. The operation for the cutting out may referred to as a trimming operation or an operation for mask processing. The mask processing displays only the lesion candidate regions and does not display other regions.

The reading support function 68*b* is a function for supporting the reading of mammogram images. Such reading support function 68*b* may, for example, execute a detection function to detect lesion candidates by computer aided detection (CAD) from the target region. The detection function is an example of a detector. For example, the reading support function 68*b* may also execute a processing function to process a mammogram image in response to operations for reading the lesion candidate region. As the processing function, for example, a tone change function to change the tone of the lesion candidate region, a size change function to change the size of the lesion candidate region, and a cut-out function to cut out the lesion candidate region may be used as appropriate.

Figure 6:
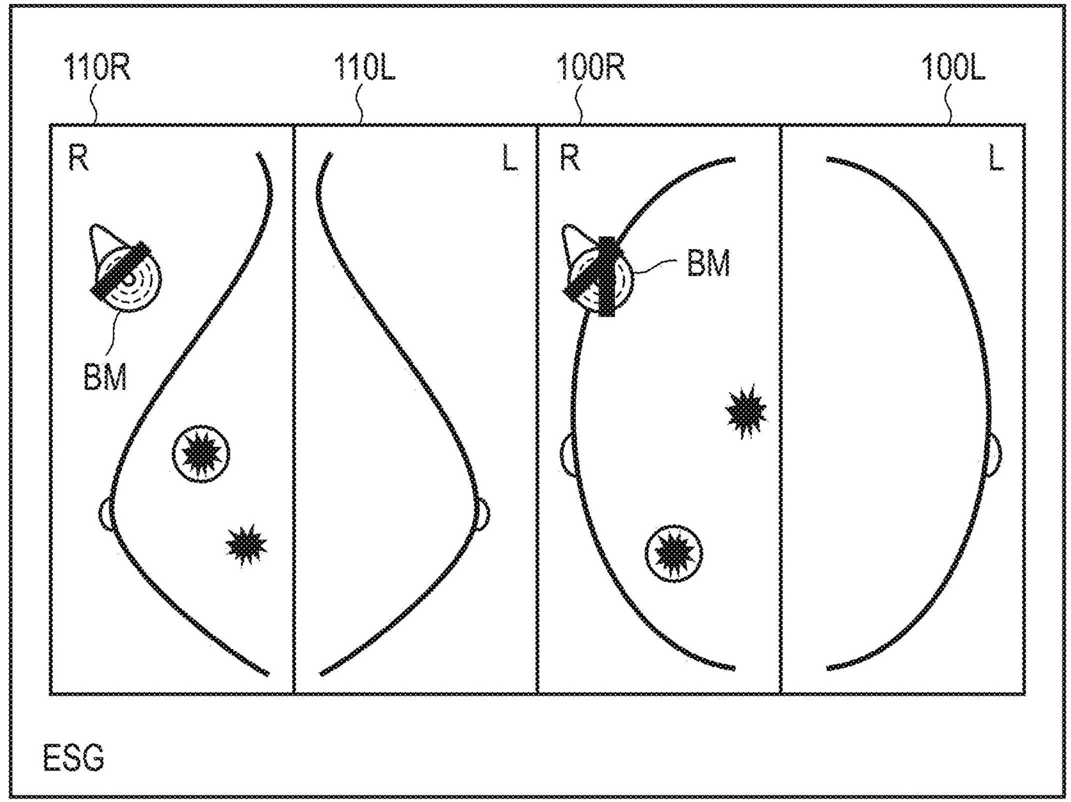
FIG. 6 is a schematic diagram illustrating echo scan guide processing in the embodiment.

The ESG processing function 68*c* executes echo scan guide (ESG) processing to link a mammogram image with an ultrasound examination. The ESG is a function that creates and displays a body mark BM (breast schematic diagram) including MLO and CC direction lines when a lesion candidate in each of the MLO and CC images is selected. For example, as shown in FIG. 6, when a lesion candidate (circled) is selected in the MLO image 110R, a body mark BM including an MLO direction line (diagonal line) corresponding to the position of the lesion candidate is created and displayed in the MLO image 110R. As shown in FIG. 6, when a lesion candidate (circled) is selected in the CC image 100R, a body mark BM including a CC direction line (vertical line) corresponding to the position of the lesion candidate and the MLO direction line described above is created and displayed in the CC image 100R. The intersection of the MLO direction line and the CC direction line corresponds to the position of the lesion candidate. Such a body mark BM containing MLO and CC direction lines is associated with the MLO and CC images and stored in the memory 62 or the image storage device 50. According to such ESG, during the ultrasound examination, the MLO and CC images and the body mark BM indicating the position of the lesion candidate can be displayed on the display 64. Therefore, the position on the breast where the ultrasound probe is to be applied can be indicated according to the lesion candidate (reading result) on the mammogram image.

Figure 7:
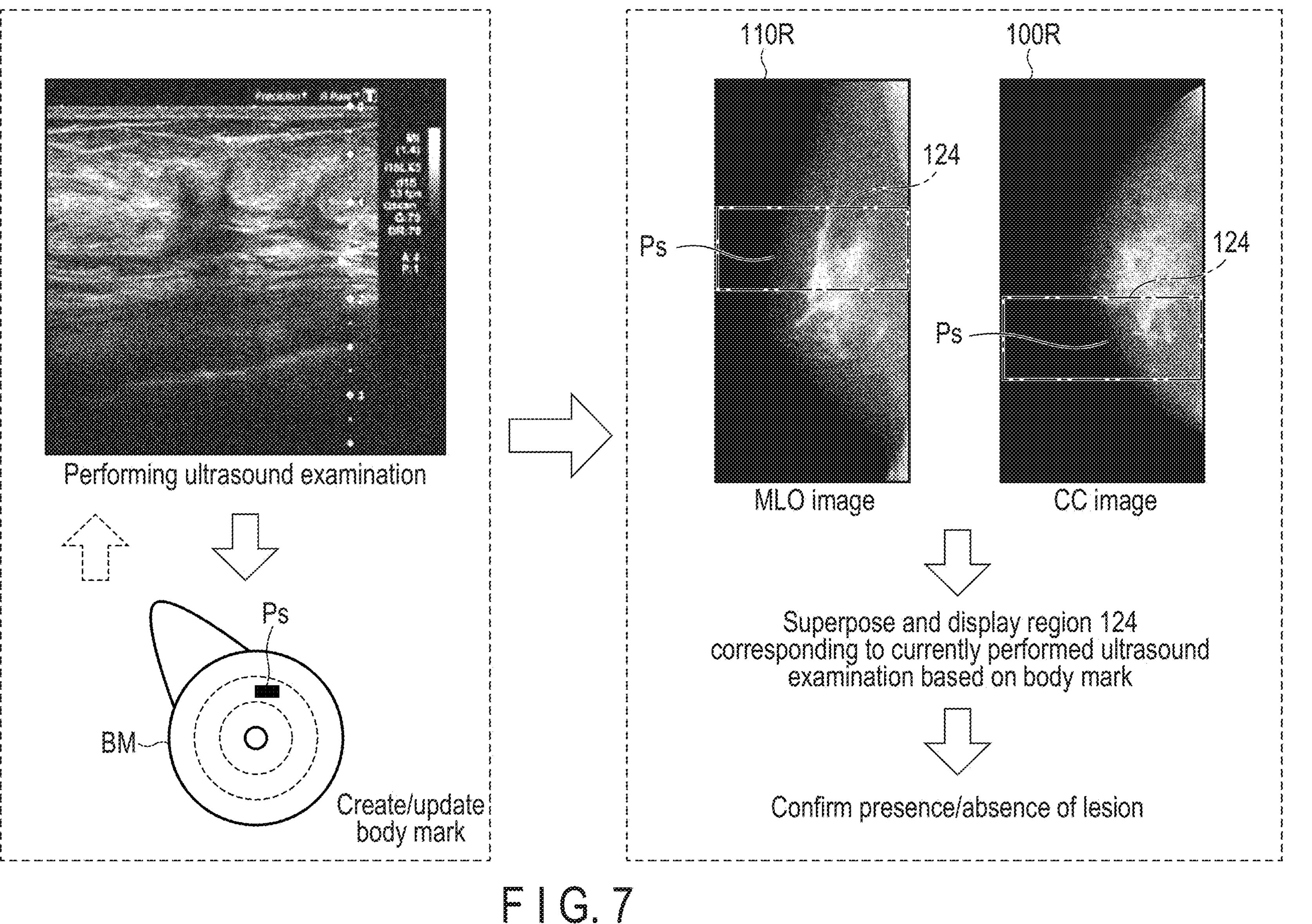
FIG. 7 is a schematic diagram illustrating cross-reference processing in body mark processing in the embodiment.
Figure 8:
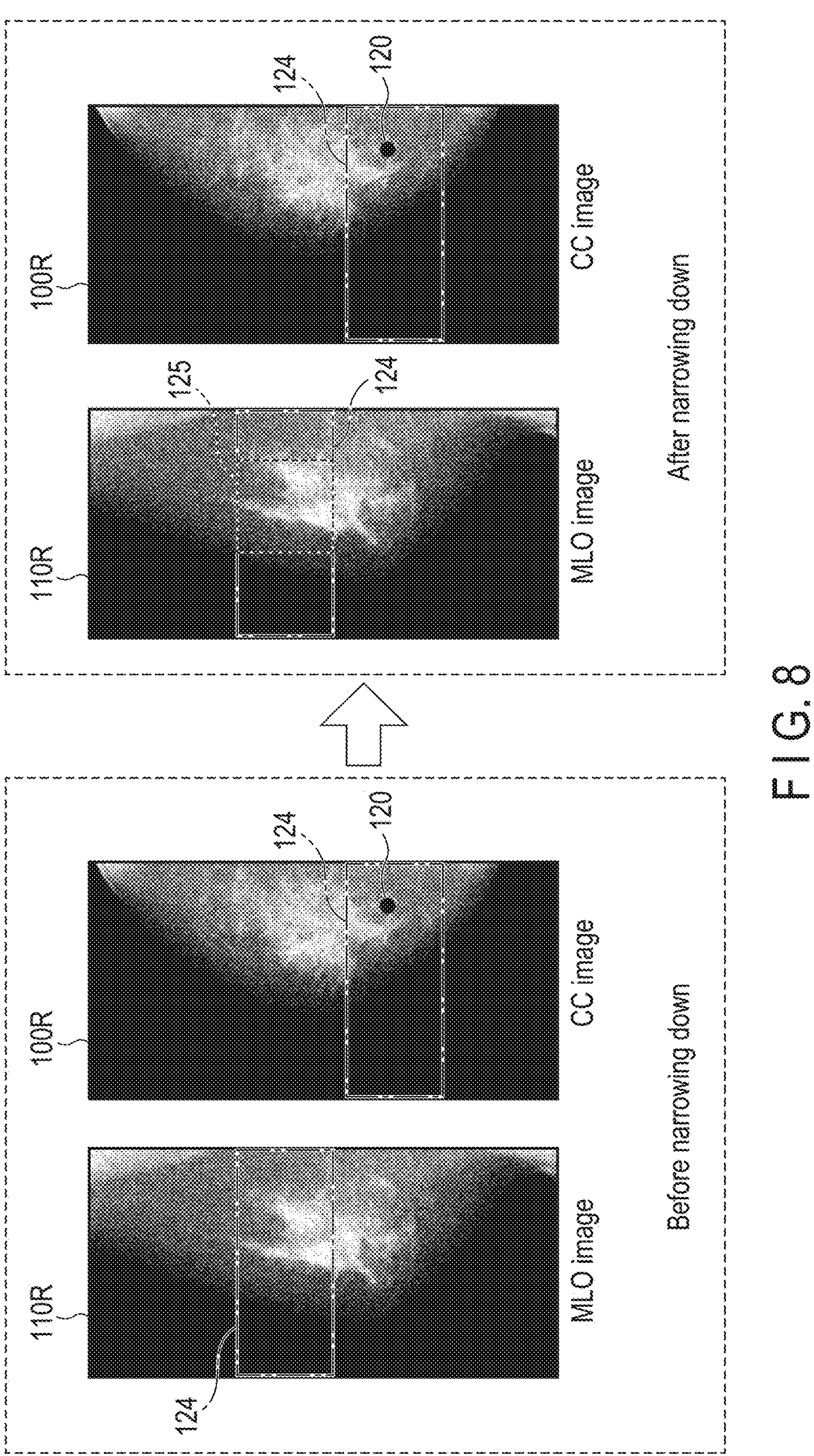
FIG. 8 is a schematic diagram illustrating the cross-reference processing in the embodiment.

The body mark search function 68*d* creates and updates the body mark BM based on the position of the ultrasound probe during the ultrasound examination. The created and updated body mark BM is associated with the ultrasound image and stored in the memory 62 or the image storage device 50. The body mark search function 68*d* also searches for a position on the mammogram image based on the position of the ultrasound probe on the body mark BM, and shows a scan region corresponding to the search result on the mammogram image. For example, as shown in FIG. 7, a region 124 corresponding to a position Ps of the ultrasound probe on the body mark BM becomes a long region (a strip region) in the vertical and horizontal directions on the MLO image 110R and the CC image 100R. Here, for example, as shown in FIG. 8, in a case where a point such as the lesion candidate 120 is selected in the region 124 of the CC image 100R, the operation restriction function 68*a* of the cross reference narrows down the target region in the other MLO image 110R to a region 125, and the operation is further limited. Note that the "body mark search" may be referred to as "body mark processing". An image set shown in FIG. 7, i.e., the ultrasound image and the MLO image 110R of the right breast and the CC image 100R of the right breast where the region 124 corresponding to the position Ps of the ultrasound probe on the body mark BM is surrounded by an enclosing frame, is stored, for example, in the memory 62 or the image storage device 50. Furthermore, an image set shown in FIG. 8, i.e., the MLO image 110R of the right breast and the CC image 100R of the right breast where the region 124 corresponding to the position Ps of the ultrasound probe on the body mark BM is surrounded by an enclosing frame, and where the region 125 corresponding to the lesion candidate 120 is further surrounded by another enclosing frame, is stored, for example, in the memory 62 or the image storage device 50.

Supplementally, the body mark search function 68*d* obtains, in advance, at the start of the ultrasound examination, imaging position information of the ultrasound image (position information of the ultrasonic probe) corresponding to the position of the patient's nipple, and associates the position of the nipple with the origin of the coordinates of the body mark. In addition to this, at the start of the ultrasound examination, the imaging position information of the ultrasound image corresponding to each position of both ends of the patient's breast may be acquired in advance, and each position of the breast may be associated with each position corresponding to both ends of the body mark. The origin of the body mark is an origin of ZY coordinates when the vertical axis is a Z axis and the horizontal axis is a Y axis in the body mark, and indicates the position of the nipple in the body mark. Each position corresponding to both ends of the body mark corresponds to each position of the two ends of the patient's breast on a circumference centered on the origin, as well as to the two ends of the breast in the mammogram image. Thus, by associating in advance the imaging position information of the ultrasound image corresponding to the characteristic positions of the breast (nipple, both ends of the breast) with the characteristic positions of the body mark (origin, both ends), it is possible to draw a mark on the body mark indicating the imaging position information of the ultrasound image (position of the ultrasound probe).

The report creation support device 70 comprises a communication interface 71, a memory 72, an input interface 73, a display 74, and processing circuitry 75.

The communication interface 71 is a circuit for connecting the report creation support device 70 to the network Nw and communicating with other devices. For example, a network interface card (NIC) can be used as the communication interface 71. In the following description, a description on the communication interface 71 intervening in the communication between the report creation support device 70 and other devices is omitted.

The memory 72 is configured by a memory that records electric information such as a read only memory (ROM), a random access memory (RAM), a hard disk drive (HDD), and an image memory, and peripheral circuits such as memory controllers and memory interfaces associated with these memories. The memory 72 stores a report creation support program of the present report creation support device and various data groups (e.g., mammogram images, ultrasound images, body marks, and past reading reports), etc. acquired to create a reading report.

The input interface 73 is realized by is a trackball, a switch button, a mouse, a keyboard, a touch pad (or a track pad) for performing input operations by touching an operation surface, and a touch panel display (or a touch screen) in which a display screen and a touch pad are integrated and the like to input various instructions, commands, information, selections, and settings from an operator (user) to a main unit of the image observation device. The input interface 73 is connected to the processing circuitry 75, converts input operations received from a user into electrical signals, and outputs the input operations received from the user to the processing circuitry 75. In this case, the input interface 73 may display a user interface (GUI: Graphical User Interface) on the display 74 for the user to input various instructions by physical operation components such as a mouse or a keyboard. Note that, in the present specification, the input interface 73 is not only limited to those with physical operation components. For example, processing circuitry of an electrical signal that receives electrical signals corresponding to input operations from an external input device provided separately from the device, and outputs these electrical signals to the processing circuitry 75 is also included in the example of the input interface 73. In the following description, an "operation of the input interface 73 by the user" is also referred to as a "user operation".

The display 74 is configured by a display body that displays medical images and reading reports created by reading the medical images, internal circuits that supply display signals to the display body, and peripheral circuits such as connectors and cables that connect the display and the internal circuits. Note that it is desirable to have more than one display 74, such as one for displaying medical images to be read and one for displaying a reading report created by reading the medical images.

The processing circuitry 75 reads the report creation support program stored in the memory 72 based on an instruction input by the user via the input interface 73, and controls the report creation support device 70 according to the program. For example, the processing circuitry 75 is a processor that realizes each function of the report creation support device 70 according to the report creation support program read from the memory 72. Here, each function includes, for example, a report creation support function 76 and a display control function 77. The report creation support function 76 includes, for example, a related image identifying function 76*a*, a key image attachment function 76*b*, and a lesion site emphasizing function 76*c*. Note that each function may be realized by being distributed across multiple processors as appropriate. For example, among each of the functions, the report creation support function 76 may be executed by a first processor, and the display control function 77 may be executed by a second processor. Alternatively, each function may be executed by an external cloud, as appropriate. For example, among each of the functions, the report creation support function 76 may be executed by an external cloud, and the display control function 77 may be executed by the processing circuitry 75. Alternatively, among each of the functions, the report creation support function 76 may be executed by the processing circuitry 75, and the display control function 77 may be executed by an external cloud.

Next, the related image identifying function 76*a*, the key image attachment function 76*b*, and the lesion site emphasizing function 76*c*, which are included in the report creation support function 76 are described in turn.

In a case where a reading order related to a medical image in which a patient's site is captured by a predetermined modality is selected from a reading order list, and a predetermined region of the medical image is specified as a region of interest (ROI), the related image identifying function 76*a* identifies a medical image corresponding to the specified region of interest as a related image from among medical images in which the patient's site is captured by a modality different from the predetermined modality described above.

For example, in a case where a reading order related to a mammogram image in which a patient's site is captured by the mammography imaging device 10 is selected from the reading order list, and a predetermined region of the mammogram image is specified as the region of interest, the related image identifying function 76*a* identifies an ultrasound image corresponding to the specified region of interest as a related image from among ultrasound images in which the patient's site is captured by the ultrasound diagnostic imaging system 30.

Alternatively, in a case where a reading order related to an ultrasound image in which a patient's site is captured by the diagnostic ultrasound device 30 is selected from the reading order list, and a predetermined region of the ultrasound image is specified as the region of interest, the related image identifying function 76*a* identifies a mammogram image corresponding to the specified region of interest as a related image from among mammogram images in which the patient's site is captured by the mammography imaging device 10.

The region of interest may be manually selected and specified by the user, or may be automatically specified based on the body mark BM associated with the medical image. The following describes a case in which the region of interest is automatically specified based on the body mark BM.

For example, in a case where a reading order related to a mammogram image captured by the mammography imaging device 10 is selected, the related image identifying function 76*a* may automatically specify a position of a lesion candidate indicated by the body mark BM that is associated to the mammogram image by the above the ESG processing function 68*c* as the region of interest. In this case, the related image identifying function 76*a* identifies the ultrasound image of when the specified region of interest (i.e., the position of the lesion candidate) was scanned by the diagnostic ultrasound device 30 as the ultrasound image corresponding to the region of interest.

In a case where a reading order related to an ultrasound image captured by the diagnostic ultrasound device 30 is selected, the related image identifying function 76*a* may automatically specify a position of the ultrasound probe indicated by the mark BM (i.e., the scan region of the diagnostic ultrasound device 30) related to the ultrasound image as the region of interest. In this case, the related image identifying function 76*a* identifies a mammogram image in which the scan region of the diagnostic ultrasound device 30 indicated by the specified region of interest is identifiably represented (e.g., an image set of the MLO image 110R and the CC image 100R shown in FIG. 7 or an image set of the MLO image 110R and the CC image 100R shown on the right side of FIG. 8) as the mammogram image corresponding to the region of interest.

Note that medical images corresponding to the read order, which are medical images to be read captured by a predetermined modality, and medical images identified as related images, which are medical images captured by a modality different from the above-mentioned predetermined modality are obtained from, for example, the image storage device 50 or the image observation device 60.

According to this function, when creating a reading report related to a medical image captured by a predetermined modality, the user can use a medical image captured by another modality and related to the medical image to be read together without having to search for such a medical image himself/herself, which can reduce the user's time and effort.

For example, according to the present function, when creating a reading report related to a mammogram image, based on the body mark BM associated with the mammogram image, an ultrasound image of when a position of a candidate lesion indicated by the body mark BM was scanned by the diagnostic ultrasound device 30 can be identified and used together with the mammogram image to reduce the time and effort required to search for the ultrasound image. Furthermore, according to the present function, when creating a reading report related to an ultrasound image, based on the body mark BM associated with the ultrasound image, it is possible to identify a mammogram image in which an enclosing frame identifiably representing a scan region of the diagnostic ultrasound device 30 indicated by the body mark BM is superposed, and use this image together with the ultrasound image, thereby reducing the time and effort required to search for the mammogram image.

The key image attachment function 76*b* is a function that automatically attaches a medical image related to a reading order selected from the reading order list (medical image to be read) and a medical image identified as a related image by the above-mentioned related image identifying function 76*a* (i.e., a medical image captured by a modality different from that of the medical image to be read) to a predetermined position in the reading report. Accordingly, the user does not have to attach the so-called key image to the reading report by himself/herself. Therefore, the time and effort required for attaching the key image can be reduced.

Note that, in the medical image to be read, the specified region of interest may be presented in an identifiable manner.

In addition, the key image attachment function 76*b* may automatically attach images of the patient in the past to a predetermined position of the reading report as key images. The images of the patient in the past includes a past medical image to which a body mark that is the same as the body mark BM corresponding to the region of interest identified by the related image identifying function 76*a* is associated, and a past medical image specified as a related image by the related image identifying function 76*a* when this medical image is the reading target (these past medical images are hereinafter collectively referred to as "past images"). This allows the user to compare the past images with the current images and perform comparative reading on the reading report. Note that the past images may be identified together with the related images by the related image identifying function 76*a* and obtained from the image storage device 50 or the image observation device 6, or may be identified separately from the related images by the key image attachment function 76*b* and obtained from the image storage device 50 or the image observation device 60.

In addition, as a function similar to the function for obtaining past images, a function may be further implemented to confirm whether or not an image of a patient that is different from the current patient, and to which a body mark that is the same as the body mark BM corresponding to the region of interest specified by the related image identifying function 76*a* is associated (hereinafter referred to as a "similar image"), exists in the image observation device 60. In such a function, in a case where it is confirmed that a similar image exists, a list of similar images is presented to the user. According to this, the user can select at least one similar image from the list of similar images to have medical images of similar cases displayed on the display 74, and perform comparative reading between the medical images and related images to be read and the similar images. Note that, in addition to the above-mentioned medical images of a patient different from the current patient, the similar images may further include medical images identified as related images by the related image identifying function 76*a* when the relevant medical images are the reading target.

Figure 9:
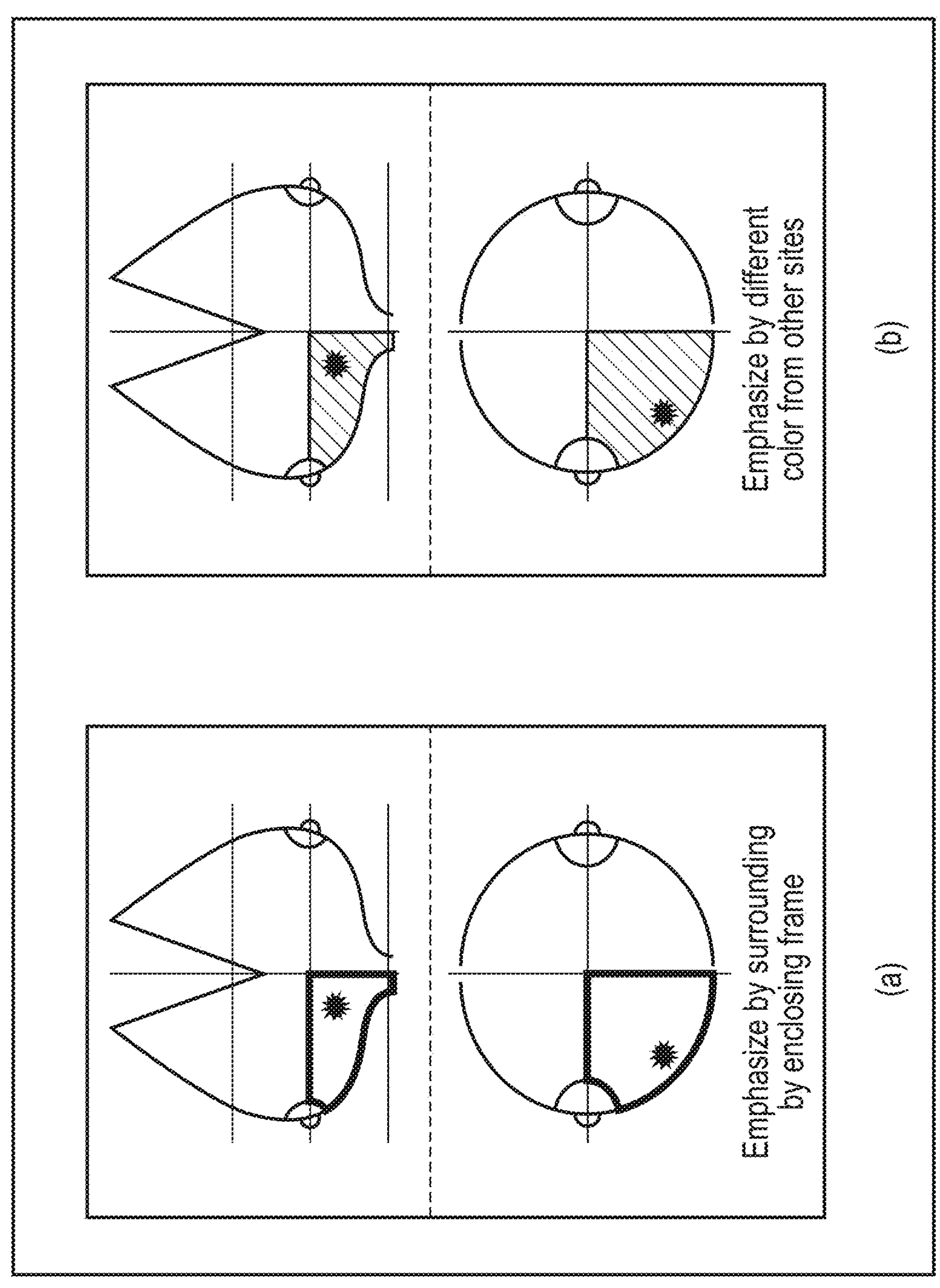
FIG. 9 is a schematic diagram illustrating an example of a lesion site enhancement function in the embodiment.

The lesion site emphasizing function 76*c* functions primarily when creating a reading report related to a mammogram image, and emphasizes the position of a candidate lesion indicated by a body mark BM associated with the mammogram image (in other words, a presumed lesion site) on a schema image related to the MLO image and the CC image. The method of emphasizing the presumed lesion site may be any method as long as the method makes the presumed lesion site identifiable from other sites. Specifically, a method of surrounding the presumed lesion site by an enclosing frame as shown in FIG. 9(*a*) and a method of showing the presumed lesion site in a different color from the other sites as shown in FIG. 9(*b*) are given as examples. This method can prevent lesion candidates from being overlooked.

Figure 10:
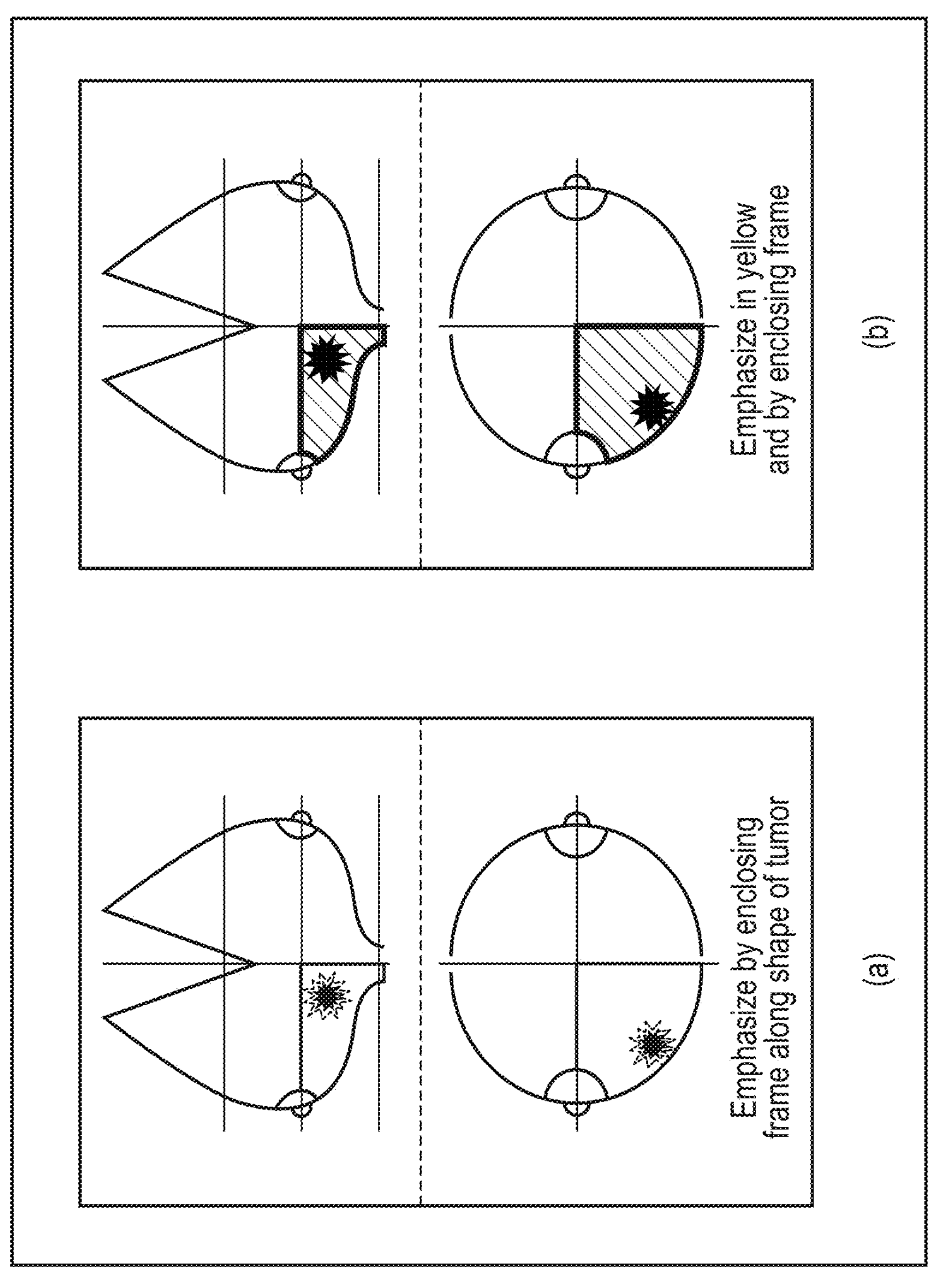
FIG. 10 is a schematic diagram illustrating an example of a lesion site enhancement function in the embodiment.
Figure 11:
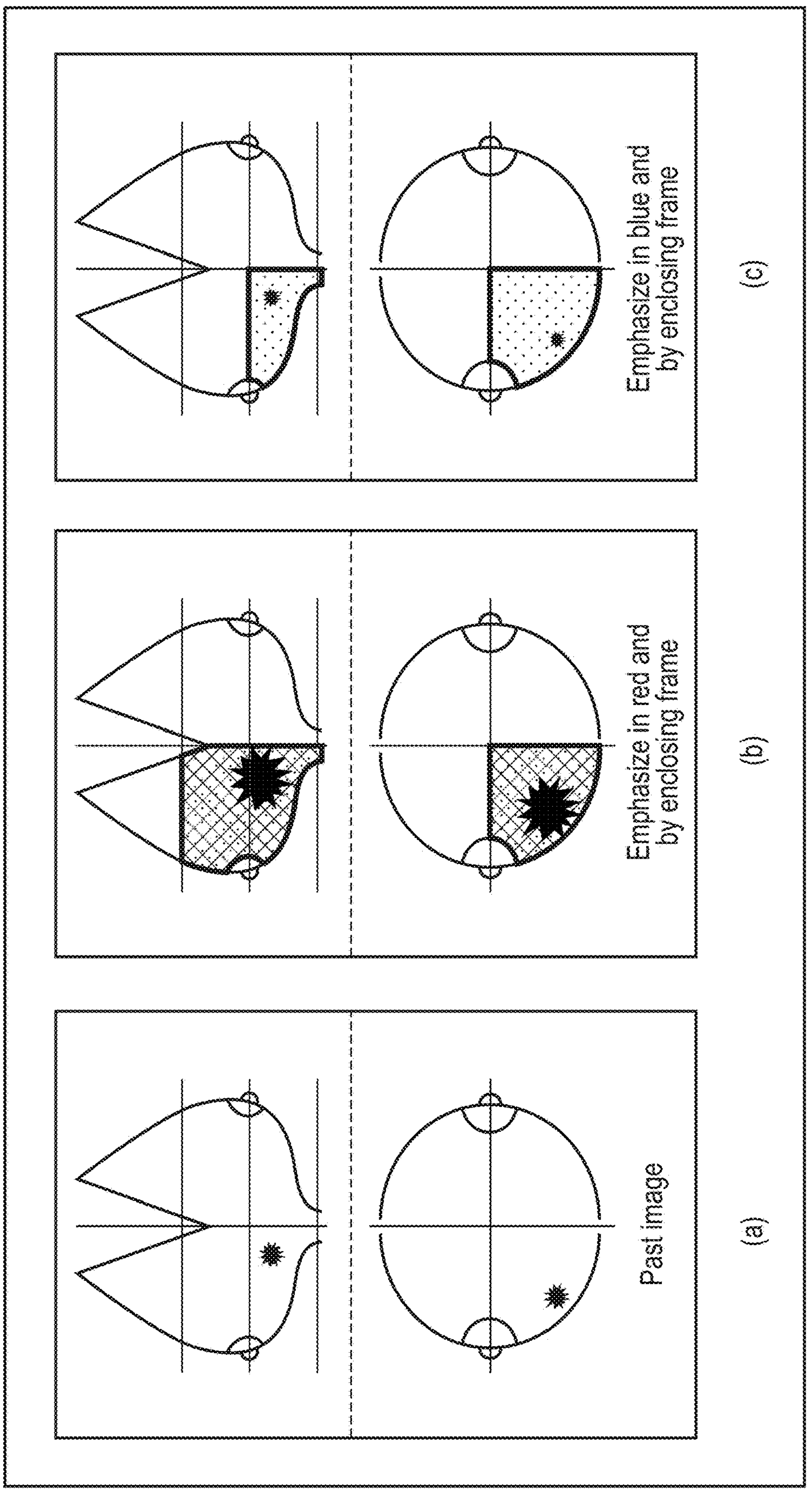
FIG. 11 is a schematic diagram illustrating an example of a lesion site enhancement function in the embodiment.

Note that, here, the lesion site emphasizing function 76*c* is described as merely emphasizing the position of lesion candidates indicated by a body mark BM (presumed lesion site) based on the body mark BM associated with the mammogram image to be read. However, it is not limited thereto. For example, the presumed lesion site may be emphasized by a method according to the shape and size of a tumor by analyzing the mammogram image to be read and identifying the shape and size of the tumor in the presumed lesion site. For example, in the case where the shape of the tumor is identified as a result of analyzing the mammogram image to be read, instead of surrounding the entire presumed lesion site, the lesion site emphasizing function 76*c* may emphasize the schema image by surrounding it by an enclosing frame along the shape of the tumor as shown in FIG. 10(*a*). Furthermore, as a result of analyzing the mammogram image to be read, in a case where the size of the tumor is identified as being large enough to reach a danger zone (in other words, larger than a preset threshold value), the lesion site emphasizing function 76*c* may emphasize the schema image by surrounding the presumed lesion site by an enclosing frame and also presenting it in yellow as shown in FIG. 10(*b*). Alternatively, as a result of analyzing the mammogram image to be read, in a case where the size of the tumor is identified as being larger than that in the past image shown in FIG. 11(*a*), the lesion site emphasizing function 76*c* may emphasize the schema image by surrounding the presumed lesion site by an enclosing frame and presenting it in red as shown in FIG. 11(*b*). On the other hand, as a result of analyzing the mammogram image to be read, in a case where the size of the tumor is identified as being smaller than that in the past image shown in FIG. 11(*a*), the lesion site emphasizing function 76*c* may emphasize the schema image by surrounding the presumed lesion site by an enclosing frame and presenting it in blue as shown in FIG. 11(*c*).

The display control function 77 is a function that displays the medical image to be read and the reading report based on the result of processing by the report creation support function 76 (i.e., a reading report including at least the medical images to be read and the related images attached by the key image attachment function 76*b*) on the display 74. Note that the display control function 77 may be implemented as a function of the report creation support function 76.

The report storage device 90 is a storage device that stores the reading reports created via the report creation support device 70. The report storage device 90 may be referred to as a report server device. Details of the reading reports stored in the report storage device 90 are described below along with FIG. 12. Therefore, the detailed description thereof is omitted here.

Figure 12:
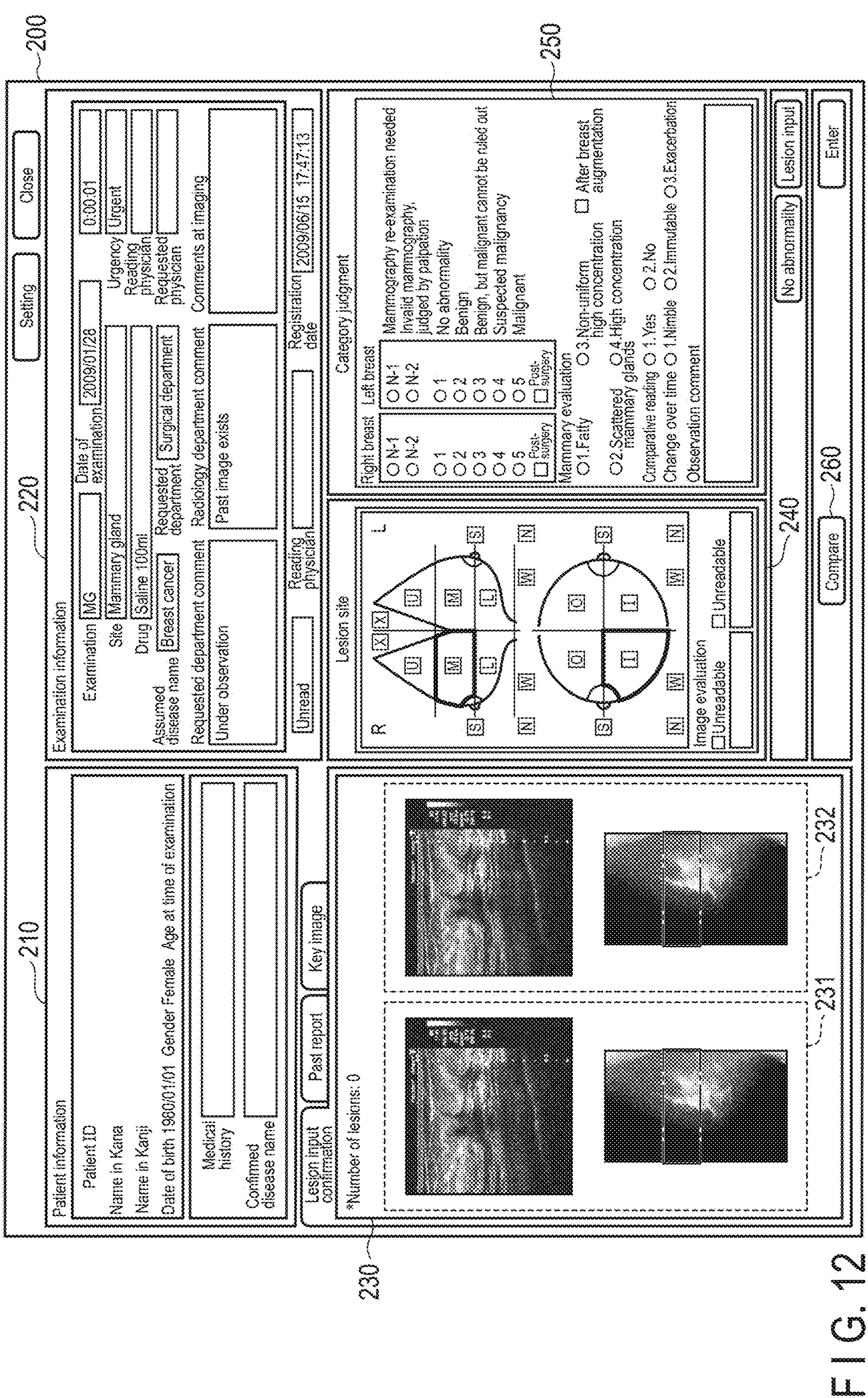
FIG. 12 is a schematic diagram illustrating a reading report screen in the embodiment.

Next, with reference to FIG. 12, a reading report screen (reading report) 200 displayed on one of the displays 74 by the display control function 77 is described. Note that FIG. 12 illustrates the reading report screen 200 that is displayed when creating a reading report related to mammogram images.

On the reading report screen 200 shown in FIG. 12, the user creates a reading report by attaching images and inputting observation comments. The created reading report is stored in memory 72 and report storage device 90.

As shown in FIG. 12, the reading report screen 200 includes, for example, a first region 210 that displays patient information, a second region 220 that displays examination information, a third region 230 that displays information related to reading, a fourth region 240 that displays information related to reading in a different format from the information displayed in the third region 230, and a fifth region 250 that displays information related to the reading in a different format than the information displayed in the third region 230 and the fourth region 240.

In the first region 210, for example, a patient ID for identifying a patient, the name of the patient identified by the patient ID, date of birth, gender and age at the time of the examination, medical history of the patient identified by the patient ID, and disease name of the patient identified by the patient ID (confirmed disease name) are displayed. The medical history and confirmed disease name are manually input by the user, for example, via the input interface 73, and information other than the medical history and disease name is automatically input based on, for example, ancillary information in the image file related to the reading order (ancillary information in a DICOM image file).

In the second region 220, for example, the content of the examination, the date and time of the examination, the subject of the examination (examination site), information on the drug used during the examination, information indicating the urgency of the reading order, the name of the physician who reads the reading order, the type of disease for which the examination was performed (assumed disease name), the section that requested the examination, the name of the physician who requested the examination, comments from the section that requested the examination, comments from the radiology department that performed the examination, and comments on the examination are displayed.

In the third region 230, information related to the lesion is displayed. Specifically, various images attached by the key image attachment function 76*b* are displayed in the third region 230. FIG. 12 exemplifies a case in which past images are displayed in a region 231 of the third region 230, and a medical image to be read (in this case, the mammogram image) and a related image (in this case, an ultrasound image corresponding to a region of interest that is specified based on a body mark BM associated with the mammogram image) are displayed in a region 232 of the third region 230. However, it is not limited to this case as long as at least the medical image to be read and the related images described above are displayed in the third region 230. Furthermore, in addition to the various images attached by the key image attachment function 76*b*, images that are attached in response to user operations (e.g., similar images) and body marks BM, etc., may be further displayed in the third region 230.

In the fourth region 240, for example, schema images that are related to MLO images and CC images, and in which a presumed lesion site is emphasized identifiably from other sites by the lesion site emphasizing function 76*c*, are displayed. By specifying a predetermined site of a schema image displayed in the fourth region 240 via the input interface 73, the user can specify the predetermined site as a region of interest for identifying a related image. Note that, since FIG. 12 shows the reading report screen 200 that is displayed when creating a reading report related to a mammogram image, a schema image related to the MLO image and the CC image is displayed in the fourth region 240. However, in the fourth region of the reading report screen that is displayed when creating a reading reported related to an ultrasound image, a body mark BM, for example, is displayed.

In the fifth region 250, information on the current reading is displayed. Specifically, the fifth region 250 displays information on the breast, information on the mammary gland, information indicating whether or not a comparative reading was performed during the current reading, information indicating changes over time, observation comments, etc. The various types of information displayed in the fifth region 250 are, for example, manually input by the user via the input interface 73. Alternatively, the various types of information displayed in the fifth region 250 may be input automatically by analyzing the mammogram image and identifying the shape and size of the tumor in the presumed lesion site in the manner described above. For example, the observation comments may be automatically input with fixed phrases corresponding to the shape and size of the tumor at the presumed lesion site. Note that the fixed phrase information related to the above fixed phrases may be stored in the memory 72 or an external cloud, for example.

Furthermore, in the reading report screen 200, in addition to the above-described first region 210 to fifth region 250, a comparison button 260 is provided. The comparison button 260 is a button for obtaining a reading report showing reading results of past images from the report storage device 90 and displaying it on the display 74. According to this, the user can read the medical images to be read and related images and create a reading report while referring to the reading report of the past images. Note that, instead of displaying the reading report of past images in response to the comparison button 260 being pressed, the reading report may be automatically obtained/displayed in a case where, for example, the presence/absence of the past image is confirmed as a result of confirming its presence.

Next, a series of processing procedures executed by the processing circuitry 75 of the report creation support device 70 when the user creates a reading report related to mammogram images is described with reference to the flowchart of FIG. 13.

First, the processing circuitry 75 displays on the display 74 a reading order list related to a reading order in response to a user operation (reading physician) (step S1). By referring to the reading order list displayed on the display 74, the user can confirm the reading order that is requested to him or her. By selecting a predetermined reading order from the reading order list displayed on the display 74, the user starts creating a reading report related to the predetermined reading order.

The processing circuitry 75 then executes the processing of creating the reading report screen 200 related to the reading order selected in response to the user operation (step S2).

Specifically, the processing circuitry 75 obtains a mammogram image to be read that is requested by the reading order selected in response to the user operation from the image storage device 50 or the image observation device 60. The processing circuitry 75 then specifies a location of the lesion candidate indicated by a body mark BM associated with the mammogram image to be read as the region of interest, and obtains the ultrasound image of when the region of interest is scanned by the diagnostic ultrasound device 30 from the image storage device 50 or the image observation device 60 as a related image (step S2-1).

Next, the processing circuitry 75 attaches the mammogram image and ultrasound image obtained by the processing in step S2-1 onto the third region 230 of the reading report screen 200. More specifically, the processing circuitry 75 attaches the mammogram image to be read and the ultrasound image identified as the related image by the processing in step S2-1 onto the third region 230 of the reading report screen 200 (step S2-2). Note that the mammogram image to be read may be attached to the third region 230 in a state where the specified region of interest is identifiable.

In addition, the processing circuitry 75 may also emphasize a presumed lesion site indicated by the body mark BM associated with the mammogram image to be read by a predetermined method on the schema image related to the MLO image the CC image displayed on the fourth region 240 of the reading report screen 200 (step S2-3).

According to the processing in steps S2-1 to S2-3 described above, the processing circuitry 75 is able to attach the mammogram image to be read and the ultrasound image of when a position of the lesion candidate which is indicated by the body mark BM associated with the mammogram image is scanned by the diagnostic ultrasound device 30 onto the third region 230 as key images, and generate the reading report screen 200 in a state where a presumed lesion site indicated by the body mark BM is emphasized by a predetermined method on the schema image related to the MLO image and the CC image displayed in the fourth region 240.

After doing so, the processing circuitry 75 displays the reading report screen 200 generated by the processing in step S2 (the processing in step S2-1 to S2-3) on the display 74 (step S3). The user creates a reading report by inputting observation comments, etc., on the reading report screen 200 displayed on the display 74 by the processing in step S3. The created reading report is stored in the memory 72 and the report storage device 90.

According to the series of processing procedures shown in FIG. 13, the burden on the user (reading physician) can be significantly reduced when creating the reading report since it is possible to omit (1) the processing of identifying/selecting an ultrasound image related to the mammogram image to be read from among ultrasound images captured by the diagnostic ultrasound device 30 by a different modality from the mammogram imaging device 10 that captured the mammogram image to be read, (2) the processing of attaching the mammogram image to be read and the ultrasound image identified as the related image onto the reading report as key images, and (3) the processing of identifying a presumed lesion site, etc.

Note that, although FIG. 13 describes a series of processing procedures executed by the processing circuitry 75 when the user creates a reading report related to mammogram images, the processing circuitry 75 executes basically the same processing when the user creates a reading report related to ultrasound images. In this case, however, as the processing corresponding to the processing in step S2-3 above, the processing circuitry 75 executes processing for displaying a body mark BM indicating a scan region of the ultrasound image to be read that is attached to the third region 230 as a key image (in other words, the body mark BM indicating the position where the ultrasound probe was applied when scanning the ultrasound image) in the fourth region 240.

According to the first embodiment described above, the report creation support device 70 comprises the related image identifying function 76*a* (identifying module) and the key image attachment function 76*b* (report creating module). When an input is received that a reading order related to a first medical image in which a patient's site is captured by a first modality is selected in response to a user operation, and a predetermined region of the first medical image is specified as the region of interest, the related image identifying function 76*a* identifies a second medical image corresponding to the specified region of interest from among the second medical images in which the patient's site is captured by a second modality which is different from the first modality. The key image attachment function 76*b* attaches the first medical image and the identified second medical image to a predetermined region of the reading report created for the reading order. According to this, when the user creates a reading report for the first medical image, the user can use the second medical image associated with the first medical image to be read without having to search for the second medical image himself/herself, thereby reducing the user's time and effort. In addition, since the user does not have to attach the key image himself/herself, the user can also reduce the time and effort required to attach the key image.

According to the first embodiment, in addition to the functions described above, the report creation support device 70 further comprises a function of further identifying a first past image, which is an image in which the same site of the same patient as that in the first medical image to be read is captured in the past by the first modality, and in which the same body mark as the body mark associated to the first medical image to be read is associated, and a second past image which is identified in the past as a second medical image corresponding to the first past image, and attaching these past images together with the current images to a predetermined region of the reading report. According to the present function, the user can compare the past images and the current images on the reading report without having to select and attach the past images. The present function is particularly useful when creating a reading report for a patient under observation.

Furthermore, according to the first embodiment, in addition to the functions described above, the report creation support device 70 further comprises the lesion site emphasizing function 76*c* (emphasizing module) which, in a case where the first medical image to be read is a mammogram image, emphasizes a site including a position of a lesion candidate indicated by a body mark associated with the mammogram image on a schema image that schematically shows the left and right breasts identifiably from the other sites. According to this function, it is possible to alert the user not to forget to read the presumed lesion site, thereby preventing the lesion from being overlooked.

Second Embodiment

A second embodiment is described below. In the first embodiment described above, processing is mainly described in which the region of interest is automatically specified based on the body mark BM associated with the mammogram image or ultrasound image to be read, the ultrasound image or mammogram image corresponding to the specified region of interest (i.e., a medical image captured with a different modality than the medical image to be read) is specified as a related image, and the medical image to be read and the related image are attached as a key image in the reading report. In addition, in the first embodiment described above, a case in which the body mark BM used to specify the region of interest is created and updated by, for example, the ESG processing function 68*c* or the body mark search function 68*d* is described.

However, in actual clinical practice, the body mark BM is often manually specified its position by the operator and added to the medical image. In such cases, the body mark BM is often not added at the exact position, and the body mark BM may not accurately indicate the position of the lesion candidate. According to this, the region of interest automatically specified based on the body mark BM may specify a region unrelated to the position of the lesion candidate, and a medical image unrelated to the position of the lesion candidate may be incorrectly identified as the related image described above. The present embodiment describes a configuration that can solve such problems.

To solve the above problem, in the medical information processing system according to the second embodiment, as shown in FIG. 14, a diagnostic ultrasound device 30 further comprises a position sensor 31 that can detect a spatial position of an ultrasound probe when capturing ultrasound images. Note that, in FIG. 14, the position sensor 31 is defined as a configuration included in the diagnostic ultrasound device 30; however, it is not limited thereto, and the position sensor 31 may be defined as a separate configuration from the diagnostic ultrasound device 30.

The position sensor 31 is configured by, for example, a set of a small magnetic sensor 31*a* attached to the ultrasound probe and a magnetic signal generator 31*b* fixed to an examination room or a diagnostic ultrasound device 30 body and indicating a reference position. The position sensor 31 detects a spatial position of the magnetic sensor 31*a* (i.e., the position of the magnetic sensor 31*a* relative to the reference position indicated by the magnetic signal generator 31*b*) by receiving a signal generated from the magnetic signal generator 31*b* by the magnetic sensor 31*a*. According to this, the diagnostic ultrasound device 30 can detect the spatial position of the ultrasound probe to which the magnetic sensor 31*a* is attached and the spatial position of the ultrasound image captured by the ultrasound probe, and further add position information indicating the spatial position of the detected ultrasound image to the ultrasound image in association with the body mark BM that was manually added by the operator.

Note that, the operator may have the ultrasound probe come in contact with a position to be a patient's landmark, then detect the spatial position of the ultrasound probe using the position sensor 31 and register the detected position in the diagnostic ultrasound device 30. In this manner, the operator may also register the spatial position of the above-mentioned landmark in the diagnostic ultrasound device 30. The landmark is desirably set at positions of bones whose positions are difficult to change, such as the central portion of the rib and the sacrum. By registering spatial positions of a plurality of landmarks by the operator, the spatial position of the patient (spatial position) can be determined. By capturing the breast by moving the ultrasound probe in a state where the spatial position of the patient is determined, the diagnostic ultrasound device 30 can capture an ultrasound image in a state where the spatial position of the ultrasound probe relative to the patient is obtained, and can further add position information indicating the correspondence between the ultrasound image and the spatial position of the patient to the ultrasound image in association with the body mark BM manually added by the operator.

On the other hand, the mammography imaging device 10 executes shape recognition processing on the captured mammogram image to detect the position of a nipple, which serves as a patient's landmark, and registers the detected position. In this manner, position information indicating the correspondence between the mammogram image and the spatial position of the patient can be further added to the mammogram image in association with the body mark BM manually added by the operator.

Note that the body mark BM may be added to a schema image by the operator. In such a case, a report creation support device 70 identifies the spatial position of the patient at which the body mark BM added by the operator is positioned based on a conversion coefficient or conversion table registered in advance (i.e., identifies the spatial position of the patient relative to the body mark BM added by the operator).

In the medical information processing system according to the second embodiment described above, in a case where a mammogram image or an ultrasound image to which a body mark BM is added is selected as a reading target, based on the position information added to each image in association with the body mark BM, it is possible to recognize the spatial position of the patient of each image to which the body mark BM is added (or recognize the spatial position of each image to which the body mark BM is added) and identify the ultrasound image or mammogram image corresponding to the recognized spatial position as a related image. Furthermore, in the medical information processing system according to the second embodiment described above, in the case where a body mark BM is added to a schema image by the operator (in other words, in the case where a body mark BM is specified by the operator), based on a conversion coefficient or conversion table registered in advance, it is possible to recognize the spatial position of the patient relative to the body mark BM and identify the ultrasound image or mammogram image corresponding to the recognized spatial position as the related image. The identified related image may be displayed on a display 74 as in the first embodiment described above, or may be attached to the reading report as a key image.

Note that, in a case where, in addition to the ultrasound image or mammogram image corresponding to the recognized spatial position, there is another ultrasound image or mammogram image corresponding to a spatial position near the recognized spatial position, all of these ultrasound images or mammogram images may be identified as the related images. In this case, a thumbnail image containing multiple ultrasound images or mammogram images identified as related images or an image showing the distribution of the multiple ultrasound images or mammogram images identified as related images may be displayed on the display 74, and the image or image distribution position that has a close positional relationship with the recognized spatial position may be displayed in an emphasized manner (highlighted) to prompt the operator to select an image with close positional relationship.

According to at least one of the embodiments described above, the burden on the radiologist can be reduced when creating the reading report.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A device, comprising:

processing circuitry configured to when receiving an input selecting a reading order related to a first medical image in which a site of a patient is captured by a first modality, specify a predetermined region of the first medical image as a region of interest, and identify a second medical image corresponding to the specified region of interest from among second medical images in which the site of the patient is captured by a second modality different from the first modality; and attach the first medical image and the identified second medical image to a predetermined region of a reading report created for the reading order, wherein the processing circuitry is further configured to specify the region of interest based on a body mark associated with the first medical image, identify the second medical image corresponding to the specified region of interest, identify a first past image, which is an image of the site of the patient that was captured in the past by the first modality and associated with a same body mark as the body mark associated with the first medical image, and identify a second past image identified in the past as a second medical image corresponding to the first past image, and display the first and second images and emphasize, in a first manner, a region presumed to have a lesion in the first and second medical images when a size of a tumor is identified as being larger than that in the past, and emphasize in a second manner different from the first manner, the region presumed to have a lesion in the first and second medical images when the size of the tumor is identified as being smaller than that in the past.

2. The device of claim 1, wherein the processing circuitry is further configured to attach the first medical image in which the specified region of interest is presented identifiably and the identified second medical image to the predetermined region of the reading report.

3. The device of claim 1, wherein the first modality is a mammography imaging device, the first medical image is a mammogram image, the second modality is a diagnostic ultrasound device, and the second medical image is an ultrasound image, and the processing circuitry is further configured to:

specify a position of a lesion candidate indicated by a body mark associated with the mammogram image as the region of interest; and identify an ultrasound image of when the specified region of interest is scanned by the diagnostic ultrasound device.

4. The device of claim 1, wherein the first modality is a diagnostic ultrasound device, the first medical image is an ultrasound image, the second modality is a mammography imaging device, and the second medical image is a mammogram image, and the processing circuitry is further configured to:

specify a position of an ultrasound probe indicated by a body mark associated with the ultrasound image as the region of interest; and identify a mammogram image that identifiably represents a scan region of when the specified region of interest is scanned by the diagnostic ultrasound device.

5. The device of claim 1, wherein the processing circuitry is further configured to attach the identified first past image and second past image to a predetermined region of the reading report.

6. The device of claim 1, wherein the processing circuitry is further configured to:

identify a past reading report created for the identified first past image and second past image; and display the past reading report on a display.

7. The device of claim 1, wherein the processing circuitry is further configured to:

identify a presence/absence of a similar image, which is an image of a different patient different from the patient and to which a same body mark as the body mark associated with the first medical image is associated; and when the similar image is present, display a list of similar images on the display.

8. The device of claim 3, wherein the processing circuitry is further configured to emphasize, on a schema image schematically showing left and right breasts, a site including a position of a candidate lesion indicated by the body mark associated with the mammogram image, identifiably from other sites.

9. A device, comprising:

processing circuitry configured to when receiving an input selecting a reading order related to a first medical image in which a patient's site of a patient is captured by a first modality, identify, based on position information associated with the first medical image and indicating a correspondence between the first medical image and a spatial position of the patient, a second medical image corresponding to the spatial position of the patient from among second medical images in which the site of the patient is captured by a second modality which is different from the first modality, and attach the first medical image and the identified second medical image to a predetermined region of a reading report created for the reading order, wherein the processing circuitry is further configured to specify the spatial position of the patient based on a body mark associated with the first medical image, identify the second medical image corresponding to the specified spatial position of the patient, identify a first past image, which is an image of the site of the patient that was captured in the past by the first modality and associated with a same body mark as the body mark associated with the first medical image, and identify a second past image identified in the past as a second medical image corresponding to the first past image; and display the first and second images and emphasize, in a first manner, a region presumed to have a lesion in the first and second medical images when a size of a tumor is identified as being larger than that in the past, and emphasize in a second manner different from the first manner, the region presumed to have a lesion in the first and second medical images when the size of the tumor is identified as being smaller than that in the past.

* * * * *